United States Patent
Ohmae et al.

(10) Patent No.: US 9,711,666 B2
(45) Date of Patent: *Jul. 18, 2017

(54) SENSOR PROVIDED WITH METAL OXIDE FILM AND USE THEREOF

(75) Inventors: Keisuke Ohmae, Shiga (JP); Tetsuya Mori, Shiga (JP); Tetsuo Hayase, Aichi (JP); Seiji Nakajima, Shiga (JP); Mariko Nishiguchi, Shiga (JP)

(73) Assignee: OMRON Corporation, Kyoto (JP)

( * ) Notice: Subject to any disclaimer, the term of this patent is extended or adjusted under 35 U.S.C. 154(b) by 356 days.

This patent is subject to a terminal disclaimer.

(21) Appl. No.: 14/002,640

(22) PCT Filed: Mar. 18, 2011

(86) PCT No.: PCT/JP2011/056630
§ 371 (c)(1),
(2), (4) Date: Aug. 30, 2013

(87) PCT Pub. No.: WO2012/124127
PCT Pub. Date: Sep. 20, 2012

(65) Prior Publication Data
US 2013/0341534 A1 Dec. 26, 2013

(30) Foreign Application Priority Data
Mar. 15, 2011 (JP) ................. 2011-057277

(51) Int. Cl.
*B32B 15/08* (2006.01)
*B32B 15/04* (2006.01)
(Continued)

(52) U.S. Cl.
CPC ............ *H01L 31/0248* (2013.01); *G01L 9/02* (2013.01); *G01L 11/02* (2013.01); *G01N 27/126* (2013.01); *G01N 33/005* (2013.01)

(58) Field of Classification Search
CPC ......... G01L 9/02; G01L 11/02; G01N 27/126; G01N 33/005; H01L 31/0248
See application file for complete search history.

(56) References Cited

U.S. PATENT DOCUMENTS 3,978,731 A 9/1976 Reeder et al.
4,719,348 A 1/1988 Saito et al.
(Continued)

FOREIGN PATENT DOCUMENTS

CN 1365135 A 8/2002
CN 1405580 A 3/2003
(Continued)

OTHER PUBLICATIONS

Shukla, Satyajit, et al. "Effect of ultraviolet radiation exposure on room-temperature hydrogen sensitivity of nanocrystalline doped tin oxide sensor incorporated into microelectromechanical systems device." Journal of applied physics 97.5 (2005): 054307.*
(Continued)

*Primary Examiner* — Robert Eom
(74) *Attorney, Agent, or Firm* — Osha Liang LLP

(57) ABSTRACT

A sensor capable of detecting light, hydrogen gas, and air pressure includes a metal oxide film produced by a process including the steps of: (a) forming an organic film by using a primer composition containing (i) an addition polymerizable compound including three or more reactive groups, (ii) an addition polymerizable compound including an acid group, and (iii) an addition polymerizable compound including a hydrophilic functional group; (b) forming a metal (M1) salt from the acid group; (c) substituting the metal (M1) salt of the acid group with a metal (M2) salt by treating the organic film with a metal (M2) ion aqueous solution; (d)
(Continued)

reducing the metal (M2) ion so that a metal film is formed on a surface of the organic film; and (e) oxidizing the metal film.

8 Claims, 5 Drawing Sheets

(51) Int. Cl.
*G01N 27/04* (2006.01)
*H01L 31/0248* (2006.01)
*G01L 9/02* (2006.01)
*G01L 11/02* (2006.01)
*G01N 27/12* (2006.01)
*G01N 33/00* (2006.01)

(56) References Cited

U.S. PATENT DOCUMENTS

| | | | |
|---|---|---|---|
| 8,071,178 B2 | 12/2011 | Nakajima et al. | |
| 8,273,461 B2 * | 9/2012 | Mori | C23C 18/14 427/256 |
| 8,273,462 B2 * | 9/2012 | Nakajima | C23C 18/06 427/256 |
| 8,361,628 B2 * | 1/2013 | Nakajima | C23C 18/06 359/838 |
| 2002/0086223 A1 | 7/2002 | Hattori et al. | |
| 2002/0094483 A1 | 7/2002 | Hattori et al. | |
| 2003/0087119 A1 | 5/2003 | Iwabuchi et al. | |
| 2003/0146709 A1 | 8/2003 | Ohta et al. | |
| 2003/0149187 A1 | 8/2003 | Kano et al. | |
| 2005/0019502 A1 | 1/2005 | Kano et al. | |
| 2007/0140908 A1 | 6/2007 | Mizuguchi | |
| 2009/0038957 A1 | 2/2009 | Sakakihara et al. | |
| 2009/0202850 A1 | 8/2009 | Mori et al. | |
| 2010/0215979 A1 | 8/2010 | Nakajima et al. | |
| 2010/0230643 A1 | 9/2010 | Nakajima et al. | |
| 2011/0122400 A1 | 5/2011 | Ono et al. | |
| 2012/0113424 A1 | 5/2012 | Suda et al. | |

FOREIGN PATENT DOCUMENTS

| | | |
|---|---|---|
| CN | 101065518 A | 10/2007 |
| JP | 60-238497 A | 11/1985 |
| JP | 62-76683 A | 4/1987 |
| JP | 1-278077 A | 11/1989 |
| JP | 5-347428 A | 12/1993 |
| JP | 7-11449 A | 1/1995 |
| JP | 09-150477 A | 6/1997 |
| JP | 2001-073159 A | 3/2001 |
| JP | 2003-013245 A | 1/2003 |
| JP | 2003-151366 A | 5/2003 |
| JP | 2003/213437 A | 7/2003 |
| JP | 2004-351722 A | 12/2004 |
| JP | 2005-248205 A | 9/2005 |
| JP | 2006-130877 A | 5/2006 |
| JP | 2007-178168 A | 7/2007 |
| JP | 2008007808 A | 1/2008 |
| JP | 2008-082842 A | 4/2008 |
| WO | 2006/132241 A1 | 12/2006 |
| WO | 2008/001611 A1 | 1/2008 |
| WO | 2010013748 A1 | 2/2010 |
| WO | 2011027899 A1 | 3/2011 |

OTHER PUBLICATIONS

Leite, E. R., et al. "A new method to control particle size and particle size distribution of SnO2 nanoparticles for gas sensor applications." Advanced Materials 12.13 (2000): 965-968.*
International Search Report issued in PCT/JP2011/056630 mailed on Jun. 28, 2011 (4 pages).
Written Opinion of the International Searching Authority issued in PCT/JP2011/056630 mailed on Jun. 28, 2011 (5 pages).
Search Report Issued in corresponding European Application No. 11861099.7, mailed Oct. 16, 2014 (12 pages).
Wei-Shan Wang et al; "A ZnO nanorod-based SAW oscillator system for ultraviolet detection"; Nanotechnology, IOP Publishing, vol. 20, No. 13, pp. 1-5; Bristol, Great Britain; Apr. 1, 2009 (5 pages).
Hopui Ho et al; "Application of spectral surface plasmon resonance to gas pressure sensing"; Optical Engineering, vol. 44, No. 12, pp. 1-6; Dec. 1, 2005 (6 pages).
International Search Report from PCT/JP2007/061896, dated Sep. 25, 2007 (4 pages).
Written Opinion from PCT/JP2007/061896, mailed Sep. 25, 2007 (3 pages).
Office Action issued in U.S. Appl. No. 12/675,579, mailed on Oct. 5, 2011 (22 pages).
Office Action issued in U.S. Appl. No. 12/675,438, mailed on Sep. 30, 2011 (18 pages).
International Search Report from PCT/JP2008/070797, mailed on Feb. 24, 2009 (5 pages).
Written Opinion from PCT/JP2008/070797, mailed on Feb. 24, 2009 (3 pages).
Office Action issued in corresponding Chinese Application No. 200880105171.3, mailed Feb. 24, 2011 (20 pages).
International Search Report from PCT/JP2008/070793, mailed on Feb. 24, 2009 (5 pages).
Written Opinion from PCT/JP2008/070793, mailed on Feb. 24, 2009 (3 pages).
Chinese Office Action issued in corresponding Chinese Patent Application No. 200880105171.3, mailed Dec. 13, 2011 (6 pages).
"New type of non-conductive electroplating NCVM," Pei Chunhua, Xiamen Technology, Issue 5 in 2007, paragraph 2 in right column of p. 41, published on Oct. 15, 2007 (3 pages).
www.iCAx.org, "Ask for the key uses of NCVM in the prior art," published on Apr. 15, 2007 (5 pages).
International Search Report from PCT/JP2009/004502, mailed on Nov. 10, 2009 (2 pages).
Written Opinion from PCT/JP2009/004502, mailed on Nov. 10, 2009 (3 pages).
Office Action issued in U.S. Appl. No. 13/059,718, mailed Mar. 14, 2012 (15 pages).
Office Action issued in U.S. Appl. No. 12/675,579, mailed Feb. 24, 2012 (17 pages).
Office Action issued in corresponding Chinese Application No. 200980132045.1, mailed on Mar. 19, 2012 (15 pages).
Office Action issued in U.S. Appl. No. 12/304,220, mailed on Sep. 29, 2011 (15 pages).

* cited by examiner

SENSOR PROVIDED WITH METAL OXIDE FILM AND USE THEREOF

BACKGROUND

Technical Field

The present invention relates to a sensor including a metal oxide film and use thereof and, more specifically, to a sensor including a metal oxide film formed by wet processing and capable of detecting light, hydrogen gas, and air pressure, a method for fabricating such a sensor, and a method for detecting a concentration of hydrogen gas etc. by using such a sensor.

Related Art

Optical sensors are widely used for optical communications compliant with IrDA (Infrared Data Association) etc., such as television and audio infrared remote controllers, office automation equipment, industrial equipment, consumer equipment, etc.

Further, hydrogen gas has drawn attention as clean and recyclable energy. However, hydrogen gas is known to be highly explosive. Therefore, in order for hydrogen gas to be widely used as a source of energy in the future, it is critical to take safety measures to safely utilize a system. As a tool that contributes to such safety measures, hydrogen gas detection sensors have increased in importance. Under such circumstances, various types of hydrogen gas detection sensor have recently been developed.

Known examples of optical sensors include an optical sensor (Patent Literature 1) using a photovoltaic element composed of a semiconductor laminate, an optical sensor (Patent Literature 2) which has an amorphous semiconductor film used as a photoconductive film and which detects a photo current based on light with which the amorphous semiconductor film has been irradiated, an optical irradiation position detection sensor (Patent Literature 3) constituted by a structure having a predetermined regularity, etc. These sensors have been developed for the purpose of, for example, making high accuracy and long-term highly-sensitive optical detection possible.

Further, known examples of hydrogen gas detection sensors include a sensor (Patent Literature 4) using a hydrogen storing alloy thin film, a sensor (Patent Literature 5) which detects a change in resistance caused by hydrogenaration of a sensing film surface having photoemissive particles dispersed thereon, etc. These sensors have been developed for the purpose of accurately measuring gas concentrations with less power consumption while keeping detection sensitivity and for stably detecting hydrogen gas leaks with reduced variation in electric conductivity.

CITATION LIST

Patent Literature 1
Japanese Patent Application Publication, Tokukaihei, No. 1-278077 A (Publication Date: Nov. 8, 1989)
Patent Literature 2
Japanese Patent Application Publication, Tokukaisho, No. 62-76683 A (Publication Date: Apr. 8, 1987)
Patent Literature 3
Japanese Patent Application Publication, Tokukaihei, No. 5-347428 A (Publication Date: Dec. 27, 1993)
Patent Literature 4
Japanese Patent Application Publication, Tokukai, No. 2008-82842 A (Publication Date: Apr. 10, 2008)
Patent Literature 5
Japanese Patent Application Publication, Tokukai, No. 2007-178168 A (Publication Date: Jul. 12, 2007)

SUMMARY

However, the optical sensor of Patent Literature 1 inevitably takes the form of a multi-layered film because it is necessary to join a p-type semiconductor and an n-type semiconductor to each other in order to generate photovoltaic power. Further, the optical sensor of Patent Literature 1 has a complex process because it requires formation of a multi-layered film on a transparent conductive film by a vacuum process with the films matched in condition to each other and also requires a resist, etching, etc. Furthermore, the use of the vacuum process may result in unsuitability for mass production with a larger diameter, high fabrication cost, and difficulty of fabricating a sensor on a flexible substrate.

The optical sensor of Patent Literature 2 is a sensor fabricated by forming a single-layer film on a substrate. However, because the film is made of an amorphous semiconductor, the film is low in stability. Therefore, the optical sensor of Patent Literature 2 requires a heating element for ensuring the stability of the film. This causes the substrate to be always subjected to heat, thus causing a low degree of freedom of substrate selectivity. Further, the formation of the film by a vacuum process may result in unsuitability for mass production with a larger diameter and high fabrication cost.

The optical irradiation position detection sensor of Patent Literature 3 has an electrode layer, made of a high electrical resistive element, which retains linearity by forming a complex and repeated structure. This allows a collected current to flow over a long distance through the electrode layer made of the high electrical resistive element, thus making it possible to obtain a large voltage drop and therefore improve measurement accuracy.

However, the optical irradiation position detection sensor of Patent Literature 3 requires a high-resistance film for increasing the accuracy of detection of a position irradiated with light, and a normal ITO film is too low in resistance, while it is difficult to increase the resistance. Further, although it is necessary to reduce the film thickness in order to obtain a high-resistance film, the use of a film with a film thickness of several nanometers to several tens of nanometers in Patent Literature 3 makes it difficult to further reduce the film thickness, thus making it difficult to reduce the size and the thickness. Further, the complicated structure may result in high fabrication cost and unsuitability for mass production with a larger diameter.

The hydrogen gas detection sensor of Patent Literature 4 using a hydrogen storing alloy thin film carries out absorption of hydrogen into a space between metal atoms and release of hydrogen from a space between metal atoms, and as such, cannot avoid degradation of metal (hydrogen embrittlement) in an alternating succession of the absorption and the release, and further may result in high fabrication cost and unsuitability for mass production with a larger diameter.

The hydrogen gas detection sensor of Patent Literature 5 is fabricated by applying photoemissive particles onto a substrate by wet processing and sintering the film thus formed. However, it is necessary to carry out heating in order to circumvent the effect of temperature dependence during use as well as during fabrication. Because the effect of heat must be taken into consideration, the availability of substrates is limited, and because it is necessary to always carry out heating, power consumption is high.

One or more embodiments of the present invention provides a sensor including a metal oxide film formed by wet processing and capable of detecting light, hydrogen gas, and air pressure and use thereof.

According to one or more embodiments of the present invention, an element includes a metal oxide film by using a fabricating method that makes it possible to achieve a primer composition containing a functional group having excellent retentivity of a metal ion, promotion of fixing the metal ion to an organic film, prevention of elution of a metal fixed to the organic film, improvement of reduction efficiency of the metal, improvement of reactivity between treatment liquids and a primer, and the like.

One or more embodiments of the present invention improves on conventional publicly-known sensors in terms of the complexity of processes, the high fabrication cost, the low degree of freedom of substrate selection, unsuitability for mass production with a larger diameter, the high power consumption, etc. can be solved at once. A sensor according to one or more embodiments of the present invention is capable of keenly detecting light, hydrogen gas, and air pressure.

That is, a sensor according to one or more embodiments of the present invention is a sensor capable of detecting light, hydrogen gas, and air pressure, the sensor including a metal oxide film produced by a process including the steps of: (a) forming an organic film by applying a primer composition onto a substrate or a film and then polymerizing the primer composition, the primer composition containing (i) an addition polymerizable compound having three or more reactive groups, (ii) an addition polymerizable compound having an acid group, and (iii) an addition polymerizable compound having a hydrophilic functional group; (b) forming a metal (M1) salt from the acid group by treating the organic film with an aqueous solution containing a metal (M1) ion; (c) substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion; (d) reducing the metal (M2) ion so that a metal film is formed on a surface of the organic film; and (e) oxidizing the metal film.

The foregoing structure allows the organic film to take a high-bulk three-dimensional structure (hereinafter referred to as "bulky structure") attributed to the addition polymerizable compound having three or more reactive groups. By taking the bulky structure, the organic film becomes capable of fixing a large number of metal (M2) ions to a space in the film.

Therefore, it is believed that a large number of metal ions can be fixed to the organic film. Further, because the structure allows a reducing agent to permeate into the organic film, it is believed that even those metal (M2) ions further inside of the organic film can be reduced.

Furthermore, the addition polymerizable compound having a hydrophilic functional group can improve the hydrophilicity of the organic film, and therefore allows various treatment liquids, i.e., the aqueous solution containing the metal (M1) ion, the aqueous solution containing the metal (M2) ion, and an aqueous solution of the reducing agent to exert their action further inside of the organic film. This allows the various treatment liquids to more effectively exert their action on the organic film.

Further, the organic film is ultraviolet curable, and therefore can also be applied to a low heat-resistance substrate.

Furthermore, in the metal salt forming step, the organic film has its acidic group turned into the metal (M1) salt, and in the metal fixing step, the organic film is treated with a metal (M2) ion aqueous solution containing a metal (M2) ion which has a less ionization tendency than the metal (M1) ion. Therefore, the difference in ionization tendency between the metal (M1) and the metal (M2) allows the metal (M2) ion to be efficiently fixed, and a metal film can be formed on a surface of the organic film. Moreover, by obtaining a metal oxide film through oxidization of the metal film, the metal film can be rendered transparent.

Because the process is a wet process, the process makes it possible to form the metal (M2) into a transparent conductive film uniformly on the substrate. Therefore, the sensor according to one or more embodiments of the present invention can be small in size and thickness and can be fabricated at low cost.

Further, because the sensor according to one or more embodiments of the present invention can be simple in structure and small in mounting area and height, it can be rendered more multifunctional than a conventional sensor, and as will be shown in Examples below, the sensor can sharply detect light, hydrogen gas, and air pressure. Furthermore, it is also easy to increase the diameter of a transparent conductive film.

Further, because the metal oxide film is constituted by fine particles of a metal oxide, the metal oxide film can be made larger in surface area more easily than a normal thin film. This makes it possible to detect a slight amount of light and hydrogen gas.

Furthermore, because the sensor according to one or more embodiments of the present invention can be fabricated by a simple process using a plating bath, for example, loss of material can be reduced.

A method for fabricating a sensor according to one or more embodiments of the present invention includes the steps of: (a) forming an organic film by applying a primer composition onto a substrate or a film and then polymerizing the primer composition, the primer composition containing (i) an addition polymerizable compound having three or more reactive groups, (ii) an addition polymerizable compound having an acid group, and (iii) an addition polymerizable compound having a hydrophilic functional group; (b) forming a metal (M1) salt from the acid group by treating the organic film with an aqueous solution containing a metal (M1) ion; (c) substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion; (d) reducing the metal (M2) ion so that a metal film is formed on a surface of the organic film; and (e) obtaining a metal oxide film by oxidizing the metal film.

Because the process according to one or more embodiments of the present invention is a wet process, the process makes it possible to form an oxide of the metal (M2) into a film uniformly on the substrate. The metal oxide film is constituted by fine particles of a metal oxide.

Therefore, the metal oxide film can be made larger in surface area more easily than a normal thin film. This makes it possible to fabricate a sensor capable of detecting a slight amount of light and hydrogen gas.

Further, because the organic film is ultraviolet curable, it does not require high-temperature treatment and can also be applied to a low heat-resistance substrate. This makes it possible to fabricate a sensor with a high degree of freedom of substrate selection.

As described above, a sensor according to one or more embodiments of the present invention is a sensor capable of detecting light, hydrogen gas, and air pressure, the sensor including a metal oxide film produced by a process including the steps of: (a) forming an organic film by applying a primer composition onto a substrate or a film and then polymerizing the primer composition, the primer composition containing (i) an addition polymerizable compound having three or more reactive groups, (ii) an addition polymerizable compound having an acid group, and (iii) an addition polymerizable compound having a hydrophilic functional group; (b) forming a metal (M1) salt from the acid group by treating the organic film with an aqueous solution containing a metal (M1) ion; (c) substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion; (d) reducing the metal (M2) ion so that a metal film is formed on a surface of the organic film; and (e) oxidizing the metal film.

This brings about an effect of achieving a multifunctional sensor capable of detecting light, hydrogen gas, and air pressure and allowing the sensor to detect a slight amount of light and hydrogen gas and a further effect of achieving reduction in size and thickness of the sensor and achieving low-cost fabrication of the sensor.

DETAILED DESCRIPTION

Figure 1:
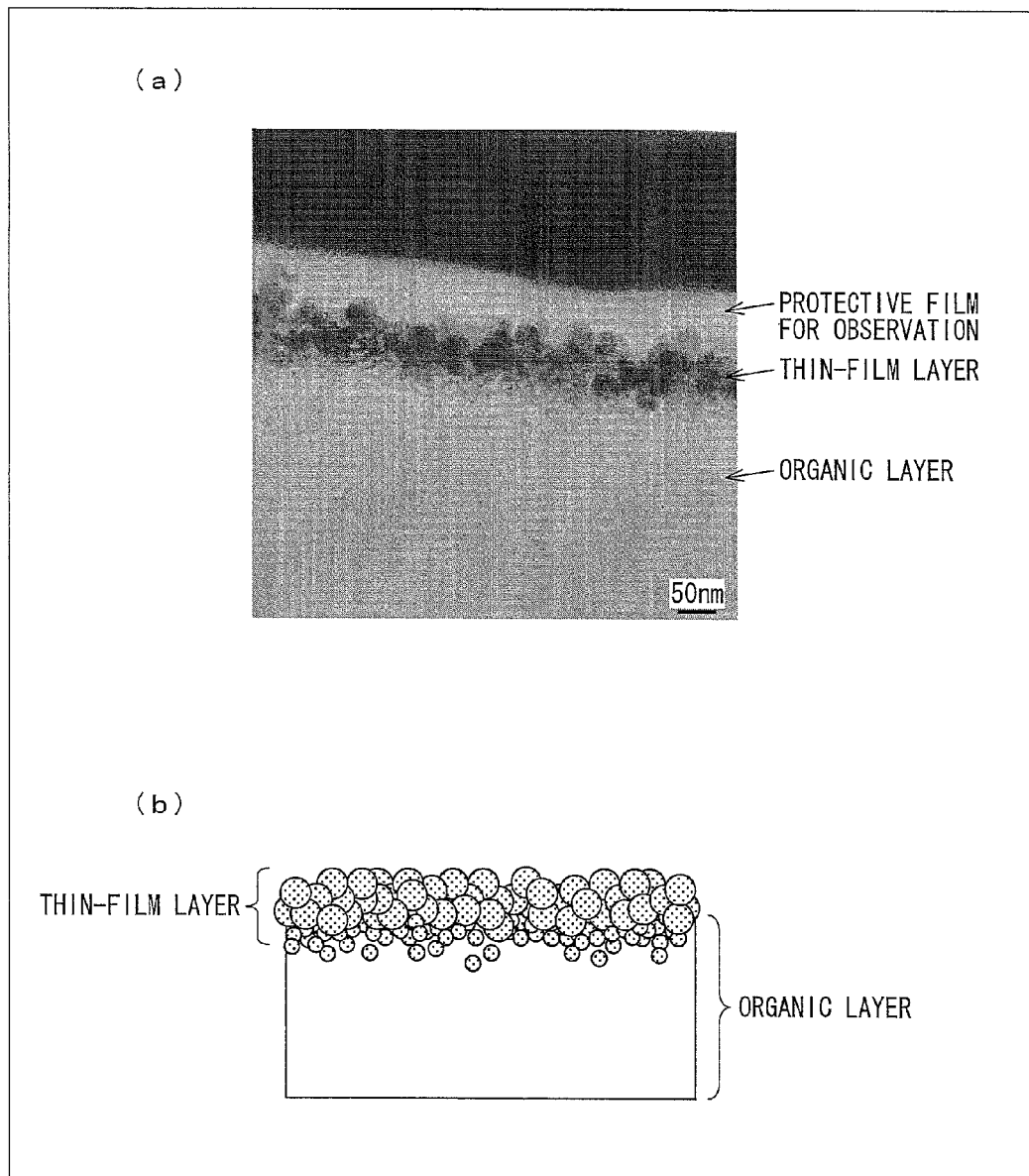
FIGS. 1(a)-(b) is a set of diagrams, the diagram 1(a) being a photograph showing a result of observation of a longitudinal section of a metal oxide film of a sensor according to an embodiment of the present invention by a transmission electron microscope, the diagram 1(b) being a schematic view of the longitudinal section.

Embodiments of the present invention are described below with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. Additionally, the present invention is not to be limited to the below embodiments. The expression "A to B" herein means "A or more to B or less".

(1. Sensor)

A sensor according to one or more embodiments of the present invention includes a metal oxide film produced by a predetermined process, and can detect light, hydrogen gas, and air pressure. First, the process is described.

The process is a process including the steps of: (a) forming an organic film by applying a primer composition onto a substrate or a film and then polymerizing the primer composition, the primer composition containing (i) an addition polymerizable compound having three or more reactive groups, (ii) an addition polymerizable compound having an acid group, and (iii) an addition polymerizable compound having a hydrophilic functional group; (b) forming a metal (M1) salt from the acid group by treating the organic film with an aqueous solution containing a metal (M1) ion; (c) substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion; (d) reducing the metal (M2) ion so that a metal film is formed on a surface of the organic film; and (e) oxidizing the metal film.

(1-1. Organic Film Forming Step)

The primer composition serves to form a primer (resin film) on a surface of which a metal (M2) ion, which is introduced in the after-mentioned metal fixing step, is deposited to form a predetermined metal film. The primer composition may further contain an addition polymerizable compound having a basic group.

The addition polymerizable compound having three or more reactive groups, the addition polymerizable compound having an acid group, the addition polymerizable compound having a hydrophilic functional group, and the addition polymerizable compound having a basic group each include a polymerizable unsaturated bond or, in particular, each include at least one polymerizable double bond per molecule. The "addition polymerizable compound" herein refers to a compound that can be addition-polymerized by activation energy such as ultraviolet rays, plasma, or an electron beam, and may be a monomer, an oligomer, or a polymer.

The "addition polymerizable compound having three or more reactive groups" is used for giving a bulky structure to the primer composition. By taking a bulky structure, the primer composition allows the organic film to have a high-bulk three-dimensional structure (bulky structure) attributed to the compound, as compared with the case of polyimide. This makes it possible to fix a large number of metal (M2) ions to the organic film in the after-mentioned metal fixing step, and to render the metal (M2) ions in the film accessible by a reducing agent or ultraviolet rays.

The term "reactive group" refers to an addition polymerizable reactive group capable of addition polymerization such as radical polymerization or cationic polymerization. Usable examples of reactive groups include, but are not to be particularly limited to, an acryloyl group, a methacryloyl group, an acrylamide group, a vinyl group, or an allyl group. Among them, according to one or more embodiments of the present invention, at least an acryloyl group and a methacryloyl group is used because they are each a functional group that easily constitutes a bulky structure. Accordingly, according to one or more embodiments of the present invention, the reactive groups of the addition polymerizable compound having three or more reactive groups includes an acryloyl group and/or a methacryloyl group.

Further, a branched structure formed by the plurality of reactive groups of the addition polymerizable compound give a bulky structure to the addition polymerizable compound. Therefore, the number of reactive groups is not to be particularly limited, as long as the number is three or more.

The addition polymerizable compound having three or more reactive groups is not particularly limited in structure, as long as the addition polymerizable compound has three or more addition polymerizable reactive groups per molecule. However, a possible example of the addition polymerizable compound having three or more reactive groups is a compound represented by general formula (1):

where n denotes three or more, R1 denotes an addition polymerizable reactive group selected from the group consisting of an acryloyl group, a methacryloyl group, an acrylamide group, a vinyl group, and an allyl group, R2 denotes any structure that includes, for example, an ester group, an alkyl group, an amide group, an ethylene oxide group, and a propylene oxide group, and R3 denotes C, an alkyl group, or C—OH.

More specific examples of the addition polymerizable compound having three or more reactive groups may include trimethylolpropane triacrylate (commercially available, for example, as TMP-A from Kyoeisha Chemical Co., Ltd.), pentaerythritol triacrylate (commercially available, for example, as PE-3A from Kyoeisha Chemical Co., Ltd.), pentaerythritol tetracrylate (commercially available, for example, as PE-4A from Kyoeisha Chemical Co., Ltd.), dipentaerythritol hexaacrylate (commercially available, for example, as DPE-6A from Kyoeisha Chemical Co., Ltd.), pentaerythritol triacrylate isophorone diisocyanate urethane prepolymer (commercially available, for example, as UA306I from Kyoeisha Chemical Co., Ltd.), dipentaerythritol pentaacrylate hexamethylene diisocyanate urethane prepolymer (commercially available, for example, as UA-510H from Kyoeisha Chemical Co., Ltd.), etc.

Further, the "addition polymerizable compound having three or more reactive groups" may be used alone or in combination of two or more types thereof.

The content of the "addition polymerizable compound having three or more reactive groups" in the primer composition is not to be particularly limited, but according to one or more embodiments of the present invention, is 1% by weight or more and 60% by weight or less or, according to one or more embodiments of the present invention, 5% by weight or more and 50% by weight or less in relation to the whole primer composition.

Increasing the content of the addition polymerizable compound causes the addition polymerizable compound to have a bulky structure that enhances the effect of fixing a metal (M2) ion by the primer composition and the effect of reducing a metal (M2) ion, but at the same time causes a decrease in the proportion of the addition polymerizable compound having an acid group, the addition polymerizable compound having a basic group, and the addition polymerizable compound having a hydrophilic functional group in the primer composition, thus reducing the efficacy of these compounds. Therefore, according to one or more embodiments of the present invention, the content of the "addition polymerizable compound having three or more reactive groups" in the primer composition falls within the aforementioned range.

The acid group in the "addition polymerizable compound having an acid group" is not to be particularly limited, as long as the acid group is capable of retaining a metal ion in the form of a salt. Possible examples of the acid group include a phenolic group, a benzoic acid group, a benzenesulfonic acid group, a carboxyl group, a sulfonic acid group, a hydroxyl group, a phthalic acid group, a salicylic acid group, an acetylsalicylic acid group, etc.

The inventors have found that a strongly acidic acid group is particularly excellent in retentivity of a metal ion and very effective in producing a metal film. Therefore, according to one or more embodiments of the present invention, the acid group is a strongly acidic acid group. According to one or more embodiments of the present invention, the strongly acidic acid group includes one or more functional groups selected from the group consisting of a carboxyl group, a sulfonic acid group, a phenolic group, a benzoic acid group, a phthalic acid group, a salicylic acid group, an acetylsalicylic acid group, and a benzenesulfonic acid group, because these groups are excellent in retentivity of a metal ion.

At least one acid group in the "addition polymerizable compound including an acid group" needs to be located at a molecular end. The "molecular end" may be an end of a main chain or an end of a side chain. Because, in the after-mentioned metal salt forming step, a metal (M1) ion needs to be trapped by a free acid group located at a molecular end of the compound, at least one of the acid groups needs to be located at a molecular end. An acid group located at a molecular end exists in a molecule as an acid group even after addition polymerization. The acid group is treated with an aqueous solution containing a metal (M1) ion, thereby forming a metal (M1) salt in the subsequent metal salt forming step.

A possible example of the "addition polymerizable compound having an acid group" is a compound represented by general formula (2) or (3):

where R1 denotes an addition polymerizable reactive group selected from the group consisting of an acryloyl group, a methacryloyl group, an acrylamide group, a vinyl group, and an allyl group, R2 denotes any structure that includes, for example, an alkyl group, an amide group, an ethylene oxide group, and a propylene oxide group, and R3 denotes either (i) a functional group having a cyclic structure, such as a phenyl group or a cyclohexyl group, or (ii) a functional group having a linear-chain structure, such as an alkyl group, or a functional group having a branched structure, such as an alkylene group.

More specific examples of the "addition polymerizable compound having an acid group" may include (meth)acrylic acid, vinyl benzenecarboxylic acid, vinyl acetic acid, vinyl sulfonic acid, vinyl benzenesulfonic acid, maleic acid, fumaric acid, an acrylic ester having a phthalic acid group, an acrylic ester having a salicylic acid group, an acrylic ester having an acetylsalicylic acid group, and vinylphenol. The "addition polymerizable compound having an acid group" may be used alone or in combination of two or more types thereof.

The "addition polymerizable compound containing an acid group" is a compound whose acid group located at a molecular end exists in a molecule not as an ester but as an acid group even after addition polymerization. That is, the "addition polymerizable compound having an acid group" is a compound that does not contain, as an acid group located at a molecular end, an ester group of the acid group.

In a case where the "addition polymerizable compound containing an acid group" does not contain, as an acid group, an ester group of the acid group, the acid group remains not as an ester but as an acid group in the organic film even after addition polymerization. The addition polymerizable compound has an acid group such as a sulfonic acid group or a carboxyl group at an end even after polymerization.

For example, HOA-MPL used in Examples is an addition polymerizable compound represented by formula 4 and corresponds to an "acrylic ester having a phthalic acid group". In formula (4), an acid group located at a molecular end is boxed. As mentioned above, the "addition polymerizable compound containing an acid group" has one or more polymerizable unsaturated bond per molecule, and in the case of HOA-MPL, addition polymerization is performed through vinyl polymerization. Therefore, the phthalic acid group of HOA-MPL is not used for polymerization, does not become an ester even after addition polymerization, and remains as a phthalic acid group in the organic film.

[Chem. 1]

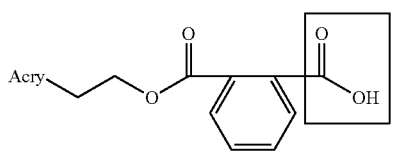

(4)

The content of the "addition polymerizable compound having an acid group" in the primer composition is not to be particularly limited, but according to one or more embodiments of the present invention, is 10% by weight or more and 90% by weight or less or, according to one or more embodiments of the present invention, 20% by weight or more and 80% by weight or less in relation to the whole primer composition.

Increasing the content of the "addition polymerizable compound having an acid group" causes the primer composition to have improved metal-ion retentivity, but at the same time causes a decrease in the content of the addition polymerizable compound having three or more reactive groups and the addition polymerizable compound having a hydrophilic functional group, thus reducing the efficacy of these compounds. Therefore, according to one or more embodiments of the present invention, the content of the "addition polymerizable compound having an acid group" falls within the aforementioned range.

The term "hydrophilic functional group" means a functional group that is highly compatible with an aqueous solution. Usable examples of the "hydrophilic functional group" include an ethylene oxide group, a propylene oxide group, an acetal group, a hydroxyl group, an ether group, etc. Among them, according to one or more embodiments of the present invention, an ethylene oxide group and a propylene oxide group are used because they are highly capable of improving the hydrophilicity of the organic film. Accordingly, according to one or more embodiments of the present invention, the hydrophilic functional group includes an ethylene oxide group and/or a propylene oxide group.

A possible example of the "addition polymerizable compound having a hydrophilic functional group" is a compound represented by general formula (5):

$$R1\text{-}R2\text{-}R1 \quad (5)$$

where R1 denotes an addition polymerizable reactive group selected from the group consisting of an acryloyl group, a methacryloyl group, an acrylamide group, a vinyl group, and an allyl group, R2 denotes a hydrophilic functional group selected from the group consisting of, for example, an ethylene oxide group, a propylene oxide group, an acetal group, a hydroxyl group, and an ether group.

More specific examples of the "addition polymerizable compound having a hydrophilic functional group" may include polyethylene glycol diacrylate, polypropylene glycol diacrylate, glycerin diacrylate, polytetramethylene glycol diacrylate, 2-hydroxypropyl acrylate, etc. The "addition polymerizable compound having a hydrophilic functional group" may be used alone or in combination of two or more types thereof.

The content of the "addition polymerizable compound having a hydrophilic functional group" in the primer composition is not to be particularly limited, but according to one or more embodiments of the present invention, is 1% by weight or more and 80% by weight or less or, according to one or more embodiments of the present invention, 5% by weight or more and 50% by weight or less in relation to the whole primer composition.

Increasing the content of the "addition polymerizable compound having a hydrophilic functional group" enhances the effect of improving the hydrophilicity of the organic film, but at the same time causes a decrease in the content of the addition polymerizable compound having three or more reactive groups and the addition polymerizable compound having an acid group, thus reducing the efficacy of these compounds. Therefore, according to one or more embodiments of the present invention, the content of the "addition polymerizable compound having a hydrophilic functional group" falls within the aforementioned range.

According to one or more embodiments of the present invention, the primer composition contains an addition polymerizable compound having a basic group. The "addition polymerizable compound having a basic group" refers to an addition polymerizable compound having one or more basic groups per molecule.

Causing the primer composition to contain an "addition polymerizable compound having a basic group" makes it possible to remarkably improve the electric conductivity of a metal film produced by the process. The "addition polymerizable compound having a basic group" is considered to bring about an effect of improving the retentivity of the metal (M1) ion to the organic film. It is considered that by improving the compatibility between the primer composition and the aqueous solution containing a metal (M1) ion and thereby facilitating the reaction between the surface of the primer composition and the aqueous solution, the retentivity of the metal (M1) ion is improved.

Therefore, the addition of the "addition polymerizable compound having a basic group" to the primer composition makes it possible to control the resistance in accordance with the electric conductivity required of the resulting metal film.

The basic group is not to be particularly limited, as long as it is a basic group capable of improving the retentivity of the metal (M1) ion to an acid group. Possible examples of the basic group include primary through tertiary amino groups, a quaternary ammonium base, a pyridyl group, a morpholino group, an anilino group, an imidazole group, a quaternary pyridinium base, etc. In particular, according to one or more embodiments of the present invention, the basic group is one or more functional groups selected from the group consisting of an amino group, a pyridyl group, a morpholino group, and an anilino group, because these groups hardly inhibit addition polymerizability.

A possible example of the "addition polymerizable compound having a basic group" is a compound represented by general formula (6):

R1-R2-R3 (6)

where R1 denotes an addition polymerizable reactive group selected from the group consisting of an acryloyl group, a methacryloyl group, an acrylamide group, a vinyl group, and an allyl group, R2 denotes any structure that includes, for example, an ester group, an alkyl group, an amide group, an ethylene oxide group, and a propylene oxide group, and R3 denotes a basic group.

More specific examples of the "addition polymerizable compound having a basic group" may include dimethylaminoethyl methacrylate, diethylaminoethyl methacrylate, N-acryloyl morpholine, N,N-dimethylacrylamide, and N-(3-dimethylaminopropyl)methacrylamide.

The content of the "addition polymerizable compound having a basic group" in the primer composition is not to be particularly limited, but according to one or more embodiments of the present invention, is 1% by weight or more and 80% by weight or less or, according to one or more embodiments of the present invention, 1% by weight or more and 50% by weight or less in relation to the whole primer composition.

Thus, the primer composition contains at least an addition polymerizable compound having three or more reactive groups, an addition polymerizable compound having an acid group, and an addition polymerizable compound having a hydrophilic functional group, and according to one or more embodiments of the present invention, also contains an addition polymerizable compound having a basic group. This allows wet processing to be carried out, unlike a sputtering method, i.e., allows the metal (M2) to be treated in a plating bath, thus achieving excellent retentivity of the metal (M2) ion.

Therefore, not only a metal film of one or more metals selected from the group consisting of indium, zinc and tin, but also a metal film of gold, silver, copper, nickel, platinum, cobalt, iron or the like can be fixed with good uniformity and high adhesiveness.

The primer composition needs only contain at least an addition polymerizable compound including three or more reactive groups, an addition polymerizable compound having an acid group, and an addition polymerizable compound having a hydrophilic functional group. The primer composition can be prepared by appropriately mixing these compounds with use of a conventionally publicly-known method. Further, the primer composition can be prepared, if necessary, by further appropriately mixing an addition polymerizable compound having a basic group.

According to one or more embodiments of the present invention, the primer composition contains a polymerization initiator in addition to the compounds. The polymerization initiator is not to be particularly limited, as long as the polymerization initiator can polymerize the primer composition. Possible examples of the polymerization initiator include a radical polymerization initiator such as a photopolymerization initiator or a thermal polymerization initiator, an ion polymerization initiator such as a cationic polymerization initiator or anionic polymerization initiator, etc. Among them, according to one or more embodiments of the present invention, the radical polymerization initiator is used, and according to one or more embodiments of the present invention, the photopolymerization initiator is used because the photopolymerization initiator does not use heat and can therefore be applied to a low heat-resistance substrate.

Examples of the photopolymerization initiator include, but are not to be particularly limited to, 2-hydroxy-2-methyl-1-phenyl-propene-1-on, 2-methyl-1-[4-(methylthio)phenyl]-2-morpholinopropene-1-on, 2,4,6-trimethylbenzoyl-diphenyl-phosphinoxide, and triphenyl sulfonyl triflate.

The thermal polymerization initiator include, but are not to be particularly limited to, cumene hydroperoxide, t-butyl hydroperoxide, benzoyl peroxide, DBU, ethylene diamine, and N,N-dimethylbenzylamine. It should be noted that these polymerization initiators may be used alone or in appropriate combination thereof.

The content of the polymerization initiator is 0.05% by weight to 10% by weight or, according to one or more embodiments of the present invention, 0.1% by weight to 8% by weight in relation to the whole primer composition.

The primer composition may contain an addition polymerizable compound (hereinafter referred to as "a further addition polymerizable compound") in addition to the aforementioned addition polymerizable compound having three or more reactive groups, the aforementioned addition polymerizable compound having an acid group, the addition polymerizable compound having a basic group, and the aforementioned addition polymerizable compound having a hydrophilic functional group. The further addition polymerizable compound is a compound which does not have an acid group or an ester group thereof but which has a polymerizable unsaturated bond or, in particular, a single polymerizable double bond per molecule. Possible examples of the further addition polymerizable compound include styrene, vinylcyclohexane, etc. According to one or more embodiments of the present invention, the content of the further addition polymerizable compound is 50% by weight or less or, according to one or more embodiments of the present invention, 30% by weight or less in relation to the whole primer composition.

The primer composition may further contain an organic solvent. Causing the primer composition to contain an organic solvent improves the coating properties of the primer composition over a substrate or a film. Usable examples of the organic solvent include, but are not to be particularly limited to, propylene glycol monomethyl ether acetate, propylene glycol monomethyl ether, cyclohexanone, butyl acetate, etc. The content of the organic solvent according to one or more embodiments of the present invention is 80% by weight or less or, according to one or more embodiments of the present invention, 30% by weight or less in relation to the whole primer composition.

Any substrate or film may be used. Examples of the substrate or film include a substrate or film made of acrylic resin, polyester resin, polycarbonate resin, polyethylene terephthalate, or epoxy resin, a glass substrate, quartz, lithium niobate, lithium tantalite, borosilicate glass, PZT, or PLZT. Because the process does not require a high-temperature treatment, the process can be applied to a wide variety of substrates or films, so that even a low heat-resistance substrate or film is sufficiently usable.

A coating method can be used as a method for applying the primer composition onto a substrate or a film, without implying any particular limitation. Possible examples include methods such as an ink-jet method, screen printing, spin coating, spray coating, and dipping.

The thickness of coating of the primer composition is not to be particularly limited, is appropriately set to fall within such a range that the thickness of the organic film after polymerization falls within the after-mentioned range.

Polymerization may be carried out, for example, by using a polymerization initiator or activation energy rays such as radiation, an electron beam, ultraviolet rays, and an electromagnetic beam. For example, in a case where a photopolymerization initiator is used, the photopolymerization initiator may be irradiated, at that surface of the substrate or film onto which the primer composition has been applied, with light having a wavelength that allows a radical to be produced by the photopolymerization initiator absorbing the light. An example of the light is ultraviolet rays.

Moreover, for example, in a case where a thermal polymerization initiator is used, the thermal polymerization initiator is heated to a temperature of, for example, 50° C. to 150° C., at which the thermal polymerization initiator can be decomposed to produce a radical.

The aforementioned polymerization causes an organic film to be formed on a substrate or a film. The film thickness of the resulting organic film is not to be particularly limited. For example, a film thickness of 0.1 μm to 1000 μm or, in particular, a film thickness of 10 μm to 500 μm is suitable.

The use of the aforementioned primer composition in the production process makes wet processing possible so that a metal film can be formed by fixing the metal (M2) onto the organic film in a simple step using a plating bath. This makes it possible to fabricate a sensor according to one or more embodiments of the present invention at low cost while reducing loss of material.

Further, in a case where any sort of pattern needs to be formed on the metal oxide film of a sensor according to one or more embodiments of the present invention, the use of the aforementioned primer composition makes it possible to form the pattern directly on an organic film in the organic film forming step without using a photolithography method. While the photolithographic method requires expensive equipment, the production process makes it possible to form a desired pattern on the organic film very easily and inexpensively by transferring the desired pattern onto the primer composition and then polymerizing the primer composition. After that, a metal film having a desired pattern can be obtained through the metal salt forming step, the metal fixing step, and the reducing step.

A method of giving such a pattern to an organic film without using a photolithography method is not to be particularly limited. However, possible examples include ink-jet printing, screen printing, and a nanoimprint method.

As used herein, the nanoimprint method is a method by which the shape of a mold having projections and depressions each having a size of tens of nanometers to hundreds of nanometers is transferred by pressing the mold a resin material applied onto a substrate.

(1-2. Metal Salt Forming Step)

The metal salt forming step is a step of forming a metal (M1) salt from the acid group by treating the organic film with an aqueous solution containing a metal (M1) ion. The treatment can easily be executed, for example, by dipping in the aqueous solution containing a metal (M1) ion a substrate or film on which the organic film has been formed or by applying the aqueous solution containing a metal (M1) ion onto a substrate or film on which the organic film has been formed.

The metal (M1) ion is a metal ion that is capable of cation exchange with a metal (M2) ion that is used for forming a metal film in the after-mentioned metal fixing step. That is, the metal (M1) ion is a metal ion that has a higher ionization tendency than the metal (M2) ion. The metal (M1) ion is not to be particularly limited, as long as it is capable of cation exchange with the metal (M2) ion. Possible examples of the metal (M1) ion include an alkali metal ion and an alkali earth metal ion. Among them, according to one or more embodiments of the present invention, the metal (M1) ion is an alkali metal ion, or according to one or more embodiments of the present invention, a potassium ion or a sodium ion in view of ease of cation exchange.

The term "ionization tendency" herein means a tendency of a metal to turn into a metal ion (positive ion) upon contact with water. The strength of an ionization tendency of a metal ion is based on the strength of a tendency of a metal to turn into the metal ion.

Examples of the aqueous solution containing a metal (M1) ion include an aqueous solution of potassium hydrate, an aqueous solution of sodium hydrate, etc. The concentration of metal (M1) ion in such an aqueous solution is not to be particularly limited, as long as a metal salt of an acid group is formed. However, in one or more embodiments of the present invention, a metal salt of an acid group can be efficiently formed even in the case of a comparatively low concentration of 0.1 to 10 M or according to one or more embodiments of the present invention, 1 to 8 M. Moreover, two or more types of metal (M1) ion may be used in one or more embodiments of the present invention. In that case, according to one or more embodiments of the present invention, the sum concentration of metal (M1) ions falls within the aforementioned range.

By treating the organic film the aqueous solution containing a metal (M1) ion, a hydrogen ion of an acid group of the organic film is substituted by the metal (M1) ion. Specifically, a hydrogen ion of an acid group, such as —COOH or —$SO_3H$, of the organic film is directly substituted by the metal (M1) ion, so that a metal salt of an acid group, such as —COOM1 or —$SO_3M1$, is formed. It should be noted that M1 denotes a metal atom of the metal (M1) ion (same applies below).

The treatment condition is not particularly limited, as long as a metal salt of an acid group is formed. The treatment temperature generally ranges from 0 to 80° C. or, according to one or more embodiments of the present invention, from 20 to 50° C., and the treatment time (dipping time) generally ranges from 1 to 30 minutes or, according to one or more embodiments of the present invention, from 2 to 20 minutes.

Further, the treatment of the acid group with the aqueous solution containing a metal (M1) ion can easily be executed by dipping in the aqueous solution a substrate or film on which the acid group has been formed or by applying the aqueous solution onto a substrate or film on which the acid group has been formed. The treatment temperature may range, for example, from 0 to 80° C. or, according to one or more embodiments of the present invention, from 20 to 50° C. The treatment time (dipping time) generally ranges from 1 to 30 minutes or, according to one or more embodiments of the present invention, from 5 to 20 minutes.

Thus, in the metal salt forming step, a hydrogen ion of an acid group are substituted by a metal (M1) ion. In a case where the addition polymerizable compound having a basic group is included as a component of the organic film, the retentivity of the metal (M1) ion to the organic film can be further improved. This is presumably because the addition polymerizable compound improves the compatibility between the surface of the primer composition and the aqueous solution containing a metal (M1) ion and thereby improves the reactivity between the primer composition and the aqueous solution.

(1-3. Metal Fixing Step)

The metal fixing step is a step of substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion.

The metal fixing step can easily be executed, for example, by dipping in a metal (M2) ion aqueous solution containing a metal (M2) ion a substrate or film having formed thereon an organic film treated with the aqueous solution containing a metal (M1) ion or by applying a metal (M2) ion aqueous solution containing a metal (M2) ion onto a substrate or film having formed thereon an organic film treated with the aqueous solution containing a metal (M1) ion.

Because the metal (M2) ion has a less ionization tendency than the metal (M1) ion, a metal (M1) salt of an acid group of the organic film is easily cation-exchanged with the metal (M2) ion, and the metal (M2) ion is introduced and fixed to the organic film.

The metal (M2) is not to be particularly limited, as long as it is capable of the cation exchange. The process according to one or more embodiments of the present invention is a process suitable as an alternative process for formation of a metal film by a sputtering method.

Usable examples of the metal (M2) include gold, silver, copper, palladium, indium, zinc, tin, nickel, platinum, cobalt, and iron. Among these metals, according to one or more embodiments of the present invention, the metal (M2) is one or more type of metal selected from the group consisting of indium, zinc, and tin.

The metal (M2) ion aqueous solution is not to be particularly limited, and a possible examples thereof is an aqueous solution of indium chloride, indium nitrate, indium acetate, indium sulfate, tin (II) chloride, tin (IV) chloride, tin acetate, tin sulfate, sodium stannate, zinc chloride, zinc nitrate, zinc sulfate, zinc acetate, zinc carbonate, gold (III) chloride, gold (I) chloride, chloroauric acid, gold acetate, silver nitrate, silver acetate, silver carbonate, silver chloride, copper nitrate, copper sulfate, copper acetate, copper carbonate, copper chloride, palladium chloride, palladium nitrate, palladium acetate, palladium sulfate, trans-diaminedichloroplatinum, cobalt chloride, cobalt nitrate, cobalt sulfate, cobalt acetate, iron (II) chloride, iron (III) chloride, iron (III) nitrate, iron (II) sulfate, iron (III) sulfate, nickel chloride, nickel nitrate, nickel sulfate, nickel acetate, or the like.

The concentration of metal (M2) ion in the metal (M2) ion aqueous solution is not to be particularly limited, as long as cation exchange is achieved. However, according to one or more embodiments of the present invention, the concentration is 5 to 500 mM or, according to one or more embodiments of the present invention, 30 to 250 mM, for example.

The treatment temperature is not to be particularly limited, as long as cation exchange is achieved, but ranges, for example, from 0 to 80° C. or, according to one or more embodiments of the present invention, from 20 to 50° C. The treatment time (dipping time) is not to be particularly limited, as long as cation exchange is achieved, but ranges, for example, from 1 to 30 minutes or, according to one or more embodiments of the present invention, from 5 to 20 minutes. Moreover, two or more types of metal (M2) ion may be used in one or more embodiments of the present invention. In that case, the sum concentration of metal (M2) ions needs only fall within the aforementioned range.

According to one or more embodiments of the present invention, the metal (M2) ion aqueous solution contains an alkali metal ion and/or an alkali earth metal ion. As mentioned above, by utilizing the difference in ionization tendency between the metal (M2) ion and the metal (M1) ion, the fixing of the metal (M2) ion to the organic film can be promoted. An alkali metal and/or an alkali earth metal have/has a very high ionization tendency. Thus, in this step, ion exchange may be further promoted by causing the metal (M2) ion aqueous solution to contain an alkali metal ion and/or an alkali earth metal ion and utilizing the difference in ionization tendency between the metal (M1) ion and the metal (M2) ion in the metal (M2) ion aqueous solution. As a result, the metal (M2) can be more efficiently fixed to the organic film.

In particular, while it has been difficult to uniformly fix one or more metals selected from the group consisting of indium, zinc, and tin by a sputtering method, the coexistence of an alkali metal ion and/or alkali earth metal ion having a high ionization tendency and a metal (M1) ion makes it possible to reduce the proportion of indium and/or the like that exist(s) as an ion(s), thus presumably promoting the fixing of the metal (M2) to the organic film.

The alkali metal and the alkali earth metal may be used alone or in combination. According to one or more embodiments of the present invention, to achieve a higher ionization tendency the alkali metal is used alone. The alkali metal and the alkali earth metal are not to be particularly limited in type, but according to one or more embodiments of the present invention, in view of a high ionization tendency, a low price, and usability, sodium and potassium are employed.

The amount of the alkali metal and/or the alkali earth metal that are/is used is not to be particularly limited, as long as the alkali metal and/or the alkali earth metal are/is compatible with the metal (M2) ion aqueous solution. For example, in a case where indium is used as the metal (M2) and sodium is used as the alkali metal and/or alkali earth metal, according to one or more embodiments of the present invention, an indium ion aqueous solution and sodium as a simple substance is used with a molar ratio of indium to sodium of 1:1.

The alkali metal and/or the alkali earth metal may be added to the metal (M2) ion aqueous solution in the form of a salt that can be ionized in the aqueous solution. For example, sodium acetate, sodium carbonate or the like may be used. The alkali metal and/or the alkali earth metal may also be added in the form of an aqueous solution of, for example, potassium hydrate, sodium hydrate or the like.

According to one or more embodiments of the present invention, the metal (M2) ion aqueous solution contains polyol. For the purpose of increasing the efficiency of film formation, according to one or more embodiments of the present invention, the metal (M2) ion concentration of the metal (M2) ion aqueous solution is as high as possible. However, in the case of a metal (M2) ion of a high specific gravity, a high concentration is likely to result in precipitation. The addition of polyol prevents the metal (M2) ion from precipitating and therefore achieves a more smooth cation exchange between the metal (M2) ion and the metal (M1) ion, thus promoting the fixing of the metal (M2) ion to the organic film.

Meanwhile, in a case where the metal (M2) precipitates despite compatibility between the metal (M2) ion and a solvent, according to one or more embodiments of the present invention, the solution is stirred for efficient cation exchange. However, when the metal (M2) ion aqueous solution contains polyol, it is possible to cause cation exchange to efficiently progress without stirring. This is very advantageous also in view of improvement in work efficiency.

The number of alcoholic hydroxyl groups that are contained in the polyol is not to be particularly limited, and may be two or more per molecule. Usable examples of the polyol include glycerin, polyethylene glycol, sorbitol, etc. Among them, according to one or more embodiments of the present invention, glycerin is used, because it is excellent in thickening property, highly effective in preventing metal (M2) ion precipitation, and excellently effective in promoting the fixing of a gold ion to the organic film.

In consideration of compatibility with the metal ion aqueous solution, according to one or more embodiments of the present invention, the amount of the polyol that is used ranges from 10 to 80% by weight in relation to the metal (M2) ion aqueous solution. The polyol needs only be mixed into the metal (M2) ion aqueous solution so as to attain such a concentration.

(1-3. Reducing Step)

The reducing step is a step of reducing the metal (M2) ion so that a metal film is formed on a surface of the organic film. That is, the reducing step is a step of reducing the metal (M2) ion introduced to the organic film in the metal fixing step and thereby causing a metal atom of the metal (M2) ion to be deposited on a surface of the organic film so that a predetermined metal film is formed.

Examples of a method of reduction include a method that is carried out by using, for example, (i) one or more reducing agent selected from the group consisting of (1) ascorbic acid, sodium ascorbate, sodium boron hydroxide, dimethylamine-borane, trimethylamine-borane, citric acid, sodium citrate, tannic acid, diborane, hydrazine, formaldehyde, and lithium aluminum hydride, (2) derivatives of the compounds of (1), and (3) sulfite salt and hypophosphite, and/or (ii) one or more reducing means selected from the group consisting of (4) ultraviolet rays, heat, plasma, and hydrogen.

The derivatives are not to be particularly limited. The (3) sulfite salt and hypophosphite are not to be particularly limited, either.

A method that involve the use of a reducing agent allows the metal (M2) ion to be reduced by bringing the surface of the organic film into contact with the reducing agent. The reducing agent is generally used in the form of an aqueous solution. Thus, the metal (M2) ion can easily be reduced by dipping in the aqueous solution of the reducing agent a substrate or film having the organic film thereon.

The concentration of the reducing agent in the aqueous solution of the reducing agent is not to be particularly limited. However, according to one or more embodiments of the present invention, the concentration of the reducing agent are not too low, because the rate of the reduction reaction tends to be too slow. Similarly, according to one or more embodiments of the present invention, the concentration of the reducing agent is not too high, because the deposited metal may drop out of the substrate or the film.

Therefore, according to one or more embodiments of the present invention, the concentration of the reducing agent is 1 to 500 mM or, according to one or more embodiments of the present invention, 5 to 100 mM. The treatment temperature during reduction is not to be particularly limited, but according to one or more embodiments of the present invention, the temperature of the aqueous solution of the reducing agent ranges from 0 to 80° C. or, according to one or more embodiments of the present invention, from 20 to 50° C. Further, the treatment time (dipping time) is not to be particularly limited, but according to one or more embodiments of the present invention, ranges from 1 to 30 minutes or, according to one or more embodiments of the present invention, from 5 to 20 minutes.

Moreover, according to one or more embodiments of the present invention, the reducing step is executed by using an alcohol and/or a surface active agent together with the reducing agent. This enhances the compatibility of the water-soluble reducing agent with the primer composition, and thus making it possible to more efficiently carry out the reduction.

The alcohol needs to be amphipathic, because it needs to be soluble in the aqueous solution of the reducing agent and, at the same time, highly compatible with the metal film and the primer composition. As long as it is amphilathic, the alcohol may be a chain alcohol, an alicyclic alcohol, or an aromatic alcohol. Usable examples of the alcohol include: a lower monovalent chain alcohol, such as ethanol, methanol, propanol, and butanol; a polyhydric alcohol, such as ethylene glycol; and an aromatic alcohol, such as benzyl alcohol; and the like.

Furthermore, the surface active agent may be cationic surface active agent, an anionic surface active agent, an ampholytic surface active agent, or a nonionic surface active agent.

Usable examples of the cationic surface active agent include: an amine salt, such as an alkylamine salt, amide bonded amine salt, and an ester-bonded amine salt; a quaternary ammonium salt, such as an alkylammonium salt, an amide-bonded ammonium salt, an ester-bonded ammonium salt, and an ether-bonded ammonium salt; a pyridinium salt, such as an alkylpyridinium salt, an amide-bonded pyridinium salt, and an ether-bonded pyridinium salt; and the like.

Usable examples of the anionic surface active agent include soap, sulfate oil, an alkyl sulfate salt, an alkyl sulfonate, an alkyl allyl sulfonate, an alkyl naphthalene sulfonate, etc.

Usable examples of the nonionic surface active agent include: an ethylene oxide surface active agent of an alkyl allyl ether type, an alkyl ether type, an alkylamine type, or a similar type; a surface active agent of a polyhydric alcohol fatty acid ester type, such as glycerin fatty acid ester, sorbitan fatty acid ester, and polyethylene glycol fatty acid ester; a surface active agent of a polyethylenimine type; a surface active agent of a fatty acid alkylolamide type; and the like.

Usable examples of the ampholytic surface active agent include a combination of a cationic surface active agent and an anionic surface active agent, a combination of a cationic surface active agent or an anionic surface active agent and a nonionic surface active agent, and the like.

The alcohol and the surface active agent may be used alone or in combination. In addition, the number of types of alcohol and surface active agent that are used may be one, two, or more.

The alcohol and/or the surface active agent need(s) only be added to the aqueous solution of the reducing agent before a substrate or a film is dipped in the aqueous solution. In consideration of compatibility with the metal ion aqueous solution, the amount of the alcohol and/or the surface active agent that are/is added ranges from 10 to 60% by weight, according to one or more embodiments of the present invention. Alternatively, the alcohol and/or the surface active agent and a primer resin composition may be applied onto a substrate or a film. In this case, in consideration of compatibility with the metal ion aqueous solution, the amount of the alcohol and/or the surface active agent that are/is used ranges from 0.01 to 10% by weight, according to one or more embodiments of the present invention.

Alternatively, in the case of a method of reduction that involves the use of ultraviolet rays, the surface of the organic film needs only be irradiated with ultraviolet rays. For example, in a case where an ultraviolet irradiation device PL16-110, manufactured by SEN Lights Corporation, is used, according to one or more embodiments of the present invention, the irradiation time ranges from 10 to 150 minutes or, in particular, from 60 to 90 minutes. In the case of reduction carried out by using such a method, the irradiation of the organic film with ultraviolet rays with use of a mask makes it possible to form a metal film having a pattern corresponding in shape to the mask. This makes it possible to easily form even a comparatively complex metal pattern. Those parts of the organic film other than the pattern can be removed by dipping the organic film, for example, in a 1% nitric acid aqueous solution or the like.

In the case of a method of reduction by heating (warming), an apparatus capable of heating, such as a hot plate or an oven, may be used to reduce the metal (M2) ion. The heating temperature according to one or more embodiments of the present invention ranges from 150 to 300° C., and according to one or more embodiments of the present invention, the heating time ranges from 5 to 60 minutes.

In the reducing step, the reducing agent may be used in combination with one or more reducing means selected from the group consisting of ultraviolet rays, heat, plasma, and hydrogen.

In an embodiment of the present invention, in a case where one or more reducing agents selected from the group consisting of the (1), (2) and (3) is used in the reducing step, according to one or more embodiments of the present invention, the metal (M2) ion is reduced in the presence of an alkali metal and/or an alkali earth metal.

Because an alkali metal and/or an alkali earth metal have a much higher ionization tendency than the metal (M2) used in one or more embodiments of the present invention, reducing the metal (M2) ion in the presence of an alkali metal and/or an alkali earth metal makes it possible to prevent ionization and elution of the metal (M2) fixed to the organic film in the metal fixing step.

That is, the alkali metal and/or the alkali earth metal used in the metal fixing step serves to promote the fixing of the metal (M2) to the organic film, while the alkali metal and/or the alkali earth metal used in the reducing step serves to prevent the metal (M2) fixed to the organic film from eluting and cause the reduction to surely progress.

The alkali metal and the alkali earth metal may be used alone or in combination. However, to achieve a higher ionization tendency according to one or more embodiments of the present invention, the alkali metal is used alone. The alkali metal and the alkali earth metal are not to be particularly limited in type, but in view of a high ionization tendency, a low price, and usability, sodium and potassium are used according to one or more embodiments of the present invention.

The amount of the alkali metal and/or the alkali earth metal that are/is used is not to be particularly limited, as long as the alkali metal and/or the alkali earth metal are/is compatible with the metal (M2) ion aqueous solution. For example, in a case where indium is used as the metal (M2) and sodium is used as the alkali metal and/or the alkali earth metal, according to one or more embodiments of the present invention, an indium ion aqueous solution and sodium as a simple substance are used with a molar ratio of indium to sodium of 1:1.

The alkali metal and/or alkali earth metal may be added to the aqueous solution of the reducing agent in the form of a salt that can be ionized in an aqueous solution. For example, sodium acetate, sodium carbonate or the like may be used. The alkali metal and/or alkali earth metal may also be added to the aqueous solution of the reducing agent in the form of an aqueous solution of, for example, potassium hydrate or sodium hydrate.

Further, in a case where the reduction is carried out by using one or more means selected from the group consisting of ultraviolet rays, heat, plasma and hydrogen, an aqueous solution of an alkali metal salt and/or an alkali earth metal salt or an aqueous solution containing an alkali metal and/or an alkali earth metal is prepared, and a substrate or film having formed thereon an organic film to which a metal (M2) has been fixed is dipped in the aqueous solution, followed by a treatment such as ultraviolet irradiation.

Normally after completion of the reduction, the substrate or the film is washed and dried. The substrate or the film may be washed with water, but according to one or more embodiments of the present invention, the substrate or the film is washed with a sulfuric acid aqueous solution so that extra metal ions can be removed. The substrate or the film may be dried by being left to stand at room temperature, but according to one or more embodiments of the present invention, the substrate or the film is dried in an atmosphere of nitrogen so that the obtained metal film can prevented from being oxidized. Further, according to one or more embodiments of the present invention, the substrate or the film is washed with water between one step and another or between one treatment and another.

(1-4. Oxidizing Step)

The oxidizing step is a step of obtaining a metal oxide film by oxidizing the metal film formed in the reducing step. The oxidizing step makes it possible to give transparency to the metal film.

In one or more embodiments of the present invention, the metal oxide film takes the form of a particulate film. According to one or more embodiments of the present invention, the metal oxide film contains metal oxide particles that are an oxide of the metal (M2) which ranges in particle diameter from 1 nm or larger to 100 nm or smaller, and that the metal oxide film be such that an average particle diameter of the metal oxide particles across a straight line becomes smaller from a surface of the metal oxide film toward the organic film, the straight line being drawn on a longitudinal section of the sensor in parallel with a surface of the substrate or film on which the organic film has been formed and connecting a left edge with a right edge of the metal oxide film.

For example, in Example 2, which will be described later, a thin-film layer having a laminate structure of indium oxide particles ranging in particle diameter from 1 nm to 100 nm was obtained with a film thickness of approximately 100 nm as shown in FIGS. 1(a) and 1(b), and a so-called gradation structure was observed in which the particle diameter becomes gradually smaller from an area near a surface of the thin-film layer toward the organic film.

FIG. 1(a) is a photograph of a result of observation of a longitudinal section of a metal oxide film of a sensor according to an embodiment of the present invention by a transmission electron microscope, and FIG. 1(b) is a schematic view of the longitudinal section.

The term "particle diameter" is intended to mean the diameter of a maximum inscribed circle with respect to a two-dimensional shape of a metal oxide particle (i.e., a particle of an oxide of the metal (M2)) as observed under a microscope. For example, in cases where the two-dimensional shape of each of the metal oxide particles constituting the metal oxide film is substantially circular, elliptic, square, or rectangular, the term "particle diameter" is intended to mean the diameter of that circle, the minor axis of that ellipse, the length of each side of that square, or the length of each of the shorter sides of that rectangle, respectively.

The term "oxide of the metal (M2) which ranges in particle diameter from 1 nm or larger to 100 nm or smaller" is intended to mean that the oxide of the metal (M2), contained in the metal oxide film, ranges in particle diameter from 1 nm or larger to 100 nm or smaller".

The particle diameter can be measured by observing a cross-section with a transmission electron microscope (TEM). Any TEM can be used without particular limitation.

The term "longitudinal section of the sensor" refers to a longitudinal section obtained by cutting a sensor according to one or more embodiments of the present invention at an angle perpendicular to the substrate or film.

The term "surface of the substrate or film on which the organic film has been formed" corresponds to a lower side of the layer described as "ORGANIC LAYER") for example in FIGS. 1(a) and 1(b) of FIG. 1. According to one or more embodiments of the present invention, the metal oxide film is such that an average particle diameter of the metal oxide particles across a straight line becomes smaller from a surface of the metal oxide film toward the organic film, the straight line being drawn on a longitudinal section of the sensor in parallel with the lower side and connecting a left edge with a right edge of the metal oxide film.

The fact that an average particle diameter of the metal oxide particles across the straight line becomes smaller from a surface of the metal oxide film toward the organic film (i.e., the so-called gradation structure) can be confirmed for example as follows:

That is, a longitudinal section of a sensor is prepared, and metal oxide particles included in an area of 1 μm×1 μm are observed in a screen image with a magnification of ×100000. Next, the average particle diameter of the metal oxide particles is obtained by calculating the average value of particle diameter. The average value of particle diameter is calculated (a) by, with reference to JIS-H0501 (method of section), drawing a straight line from a left edge to a right edge of a thin-film layer in parallel with the lower side of the layer described as "ORGANIC LAYER" in FIG. 1(b) at a position of substantially 20 nm from the surface of the thin-film layer toward the organic film in such a longitudinal section of the thin film as that shown in FIGS. 1(b) and (b) by dividing the length of the straight line by the number of particles across the straight line.

Furthermore, the average particle diameter of the metal oxide particles is similarly obtained similarly drawing a straight line further toward the organic film from the surface of the thin film. This method makes it possible to confirm that the average particle diameter becomes smaller from a surface of the metal oxide film toward the organic film.

The term "across the straight line" means overlapping of at least part of the metal oxide particles with the straight line on the longitudinal section.

Further, for example, in such a case that as shown in FIG. 1(a) where the thin-film layer is inclined with respect to the lower side of the layer described as "ORGANIC FILM" in the drawing, the average particle diameter needs only be obtained by (a) rotating the thin-film layer for convenience so that the thin-film layer is substantially parallel to the lower side and (b) drawing a straight line as described above.

A film thickness of the metal oxide film can be controlled, for example, by appropriately adjusting the concentration of the aqueous solution containing a metal (M1) ion, the treatment temperature, and the treatment time in the metal salt forming step; the concentration of the aqueous solution containing a metal (M2) ion, the treatment temperature, and the treatment time in the metal fixing step; and the concentration of the reducing agent, the treatment temperature, the treatment time, etc. in the reducing step.

The film thickness can be measured by observing a longitudinal section of a sensor according to one or more embodiments of the present invention (e.g., the longitudinal section shown in FIGS. 1(a) and 1(b)) with a TEM or the like, and although not particularly limited, for the purpose of obtaining a high-resistance film, according to one or more embodiments of the present invention, the film thickness is approximately 50 nm or greater to 100 nm or smaller.

Although the foregoing description has been given by taking FIGS. 1(a) and 1(b) as an example, the sensor shown in FIGS. 1(a) and 1(b) is merely an example.

Because a sensor according to one or more embodiments of the present invention is fabricated by wet processing as described above, the metal oxide film of the sensor takes a laminate structure of an oxide of the metal (M2) which ranges in particle diameter from 1 nm or larger to 100 nm or smaller, thus taking the gradation structure. As a result, the metal oxide film has its tissue sparser than that of a metal film produced by a technique such as sputtering, and therefore has a higher electric resistance than the metal film does.

Further, because the metal oxide film can be formed directly on the organic film, the sensor according to one or more embodiments of the present invention can be made smaller in size and thickness and made larger in diameter.

A sensor according to one or more embodiments of the present invention needs only include a metal oxide film produced by the process. The oxide metal film is constituted by metal oxide particles laminated on the organic film, and some of the metal oxide particles may exist in the state of being embedded in the organic film. Besides the metal oxide film, a member such as an electrode may be included as needed.

(1-5. Detection Etc. By a Sensor According to One or More Embodiments of the Present Invention of Irradiation with or Stoppage of Light)

The inventors of the present invention evaluated the properties of a film or substrate (hereinafter referred to as "element") having formed thereon the organic film and metal oxide film produced by the aforementioned process including the organic film forming step, the metal salt forming step, the metal fixing step, the reducing step, and the oxidizing step, and found that the element exhibits such peculiar behavior that the element abruptly decreases in resistance upon being irradiated with light in the atmosphere and gradually recovers in resistance after completion of the irradiation.

Having focused attention on such behavior, the inventors of the present invention found that the element can be used as an optical sensor capable of detecting irradiation with or stoppage of light. That is, as will be shown in Examples below, irradiation with or stoppage of light can be detected by detecting a difference between a resistance indicated by the sensor during the irradiation of the sensor with the light and a resistance indicated by the sensor after the stoppage of the light.

Therefore, a method for detecting irradiation with or stoppage of light includes the steps of: (a) irradiating a sensor according to one or more embodiments of the present invention with light; (b) stopping irradiating the sensor with the light; and (c) detecting a difference between a resistance indicated by the sensor during the irradiation of the sensor with the light and a resistance indicated by the sensor after the stoppage of the light. It should be noted that in this specification, the element is sometimes referred to simply as "sensor".

Further, the intensity of light which the sensor has been irradiated can also be detected by examining a correlation between the intensities of various beams of irradiation light and the trend of changes in resistance after the stoppage of the irradiation and thereby creating a calibration curve. Therefore, the expression "capable of detecting light" encompasses detecting the intensity of irradiation light in addition to detecting irradiation with or stoppage of light.

Further, the inventors of the present invention found that the element exhibits such behavior that the element abruptly decreases in resistance upon being irradiated with light in an atmosphere of hydrogen gas and continues to decrease in resistance even after completion of the irradiation. Having focused attention on this behavior, which is different from that exhibited in the atmosphere, the inventors of the present invention found that the element can be used as a hydrogen gas detection sensor capable of measuring hydrogen gas. That is, the presence or absence of hydrogen gas in the environment can be detected by detecting a difference between a resistance indicated by the sensor during the irradiation of the sensor with the light and a resistance indicated by the sensor after the stoppage of the light.

Therefore, a method for detecting hydrogen gas includes the steps of: (a) irradiating a sensor according to one or more embodiments of the present invention with light in an hydrogen gas atmosphere; (b) stopping irradiating the sensor with the light; and (c) detecting a difference between a resistance indicated by the sensor during the irradiation of the sensor with the light and a resistance indicated by the sensor after the stoppage of the light.

Further, the intensity of light which the sensor has been irradiated can also be detected by examining a correlation between various hydrogen gas concentrations and the trend of changes in resistance after the stoppage of the irradiation of the element with light and thereby creating a calibration curve. Therefore, the expression "capable of detecting hydrogen gas" encompasses detecting a hydrogen gas concentration in addition to detecting the presence or absence of hydrogen gas.

Furthermore, the inventors of the present invention found that the behavior of the sensor recovering in resistance after the stoppage of the irradiation of the sensor with light varies depending on air pressures. That is, as will be shown in Examples below, irradiation with and stoppage of light were performed on the element under the same condition in different atmospheric pressures, and as a result, it was found that a higher atmospheric pressure leads to a higher rate of recovery of resistance.

Having focused attention on this, the inventors of the present invention found that the element can be used as an air pressure sensor capable of measuring air pressure. That is, air pressure can be measured by placing the element under different atmospheric pressures, examining, under each of the atmospheric pressures, a correlation between the atmospheric pressure and a time of recovery of resistance after the stoppage of the irradiation of the element with light, and thereby creating a calibration curve.

Therefore, a method for measuring air pressure includes the steps of: (a) irradiating a sensor according to one or more embodiments of the present invention with light under different atmospheric pressures; (b) stopping irradiating the sensor with the light; and (c) detecting, under each of the atmospheric pressures, a difference between a resistance indicated by the sensor during the irradiation of the sensor with the light and a resistance indicated by the sensor after the stoppage of the light.

The term "time of recovery of resistance" refers to a period of time between a point in time where the sensor starts to exhibit a rise in resistance after stopping being irradiated with light and a point in time where the resistance recovers to a given resistance that has been arbitrarily set. The time of recovery varies depending on the atmospheric pressure of the environment in which the sensor is placed. For example, in FIG. 6, which will be described later, the time it takes for the resistance to recover to approximately 40 k$\Omega$ is approximately 40 seconds in a case where the atmospheric pressure is 10 MPa, approximately 48 seconds in a case where the atmospheric pressure is 1 MPa, and approximately 53 seconds in a case where the atmospheric pressure is 0.1 MPa. The step of "detecting, under each of the atmospheric pressures, a difference between a resistance indicated by the sensor during the irradiation of the sensor with the light and a resistance indicated by the sensor after the stoppage of the light" is for example a step of detecting the time of recovery.

The term "under different atmospheric pressures" means atmospheric pressures in different environments. The number of such environments is not to be particularly limited; however, a larger number of such environments desirably increases accuracy of the calibration curve.

Further, based on such a feature that a higher atmospheric pressure leads to a higher rate of recovery of resistance, a sensor according to one or more embodiments of the present invention can be used as a water depth measuring sensor as will be described in Example 5 below. A water depth measuring sensor according to one or more embodiments of the present invention includes: a sensor according to one or more embodiments of the present invention; and an elastic body, the water depth measuring sensor being obtained by encapsulating the sensor in the elastic body.

According to one or more embodiments of the present invention, the intensity of light with which a sensor according to one or more embodiments of the present invention is irradiated is in the range of 0.1 mW/cm$^2$ to 1 W/cm$^2$. Further, according to one or more embodiments of the present invention, that part of a surface of the sensor which faces a light source is evenly irradiated with light.

A possible reason why the resistance of a sensor according to one or more embodiments of the present invention fabricated by the method exhibits the aforementioned behavior in the atmosphere and in an atmosphere of hydrogen gas is that the metal oxide film of the sensor according to one or more embodiments of the present invention has sparse tissue unlike a metal film produced by a method such as sputtering, takes a laminate structure of an oxide of the metal (M2) which ranges in particle diameter from 1 nm or larger to 100 nm or smaller, and takes the gradation structure.

A sensor according to one or more embodiments of the present invention has a uniform metal oxide film formed by wet processing by the aforementioned production process, and therefore does not require a multi-layered film. This makes it possible to inexpensively provide a sensor that is small in size, thin in thickness, and large in diameter. Further, because no heating is required during fabrication or during use, the degree of freedom of substrate selection is high, and power consumption can be reduced. Furthermore, because hydrogen binds to the metal oxide film as in the case of a chemical reaction, there occurs no degradation in metal due to repetition of absorption of hydrogen into a space between metal atoms and release of hydrogen from a space between metal atoms.

A sensor according to one or more embodiments of the present invention is configured such that: the metal oxide film contains metal oxide particles that are an oxide of the metal (M2) which ranges in particle diameter from 1 nm or larger to 100 nm of smaller; and the metal oxide film is such that an average particle diameter of the metal oxide particles across a straight line becomes smaller from a surface of the metal oxide film toward the organic film, the straight line being drawn on a longitudinal section of the sensor in parallel with a surface of the substrate or film on which the organic film has been formed and connecting a left edge with a right edge of the metal oxide film.

Thus, according to one or more embodiments of the present invention, the metal oxide film takes a so-called gradation structure in which the metal oxide particles become larger in average particle diameter toward an area near a surface of the film. The metal oxide film has its tissue sparser than that of a metal film produced by a method such as sputtering, and can therefore be a film that is high in electric resistance. Further, it is estimated that such a structural feature enables the sensor according to one or more embodiments of the present invention to serve as an optical sensor, a hydrogen gas detection sensor, or an air pressure sensor that has a high sensitivity and rarely malfunctions, as will be described in Examples below.

A sensor according to one or more embodiments of the present invention is configured such that the acid group includes one or more functional groups selected from the group consisting of a phenolic group, a benzoic acid group, a phthalic acid group, a salicylic acid group, an acetylsalicylic acid group, and a benzenesulfonic acid group.

Because these functional groups are highly acidic and include electron attracting groups, an acid group including these functional groups facilitate ion exchange between the metal (M1) ion and the metal (M2) ion, and further serves as a group to which the metal (M2) is easily fixed. Therefore, the foregoing configuration can provide a sensor having a higher rate of fixing of an oxide of the metal (M2).

A sensor according to one or more embodiments of the present invention is configured such that at least one of the reactive groups includes an acryloyl group and/or a methacryloyl group.

An acryloyl group and/or a methacryloyl group are/is a functional group(s) that easily constitutes a bulky structure, and can therefore structure an organic film so that a larger number of metal ions can be fixed, thus making it easy for a reducing agent to permeate further into the organic film.

This makes it seem that those metal (M2) ions further inside of the organic film can be reduced. Therefore, the foregoing configuration can provide a sensor having a higher rate of fixing of an oxide of the metal (M2).

A sensor according to one or more embodiments of the present invention is configured such that the hydrophilic functional group includes an ethylene oxide group and/or a propylene oxide group.

Among hydrophilic functional groups, ethylene oxide group and propylene oxide group have the especially superior ability to improve the hydrophilicity of the organic film, and therefore allow various treatment liquids (the aqueous solution containing the metal (M1) ion, the aqueous solution containing the metal (M2) ion, and an aqueous solution of the reducing agent) to exert their action further inside of the organic film. Therefore, the foregoing configuration can provide a sensor having a higher rate of fixing of an oxide of the metal (M2).

A sensor according to one or more embodiments of the present invention is configured such that the metal (M1) is potassium or sodium.

Potassium or sodium has a very great ionization tendency and therefore much different in ionization tendency from the metal (M2), and as such, makes it easy for the metal (M2) to be fixed in the metal fixing step. Therefore, the foregoing configuration can provide a sensor having a higher rate of fixing of an oxide of the metal (M2).

A sensor according to one or more embodiments of the present invention is configured such that the metal (M2) is at least one metal selected from the group consisting of indium, zinc and tin.

These metals are widely used as materials for transparent conductive films. The foregoing configuration can impart good in-plane uniformity and adhesiveness to transparent conductive films made of these metals, and therefore can improve efficiency in the use of the metals. Therefore, the foregoing configuration can provide a sensor having a higher rate of fixing of oxides of these metals.

A water depth measuring sensor according to one or more embodiments of the present invention includes: a sensor according to one or more embodiments of the present invention; and an elastic body, the water depth measuring sensor being obtained by encapsulating the sensor in the elastic body.

According to the foregoing configuration, the elastic body shrinks due to changes in ambient water pressure with increasing water depth, so that there is a change in air pressure inside of the elastic body. Accordingly, the air pressure inside of the elastic body can be measured by irradiating the sensor according to one or more embodiments of the present invention with light at a point where the water depth needs to be measured and detecting an inclination of recovery of the resistance of the sensor according to one or more embodiments of the present invention after stopping irradiating the sensor according to one or more embodiments of the present invention with light, and the water depth at the point can be measured on the basis of a correlation between the air pressure and the water depth.

A method for detecting irradiation with or stoppage of light according to one or more embodiments of the present invention includes the steps of: (a) irradiating a sensor according to one or more embodiments of the present invention with light; (b) stopping irradiating the sensor with the light; and (c) detecting a difference between a resistance indicated by the sensor during the irradiation of the sensor with the light and a resistance indicated by the sensor after the stoppage of the light.

A method for detecting hydrogen gas according to one or more embodiments of the present invention includes the steps of: (a) irradiating a sensor according to one or more embodiments of the present invention with light in an hydrogen gas atmosphere; (b) stopping irradiating the sensor with the light; and (c) detecting a difference between a resistance indicated by the sensor during the irradiation of the sensor with the light and a resistance indicated by the sensor after the stoppage of the light.

A method for measuring air pressure according to one or more embodiments of the present invention includes the steps of: (a) irradiating a sensor according to one or more embodiments of the present invention with light under different atmospheric pressures; (b) stopping irradiating the sensor with the light; and (c) detecting, under each of the atmospheric pressures, a difference between a resistance indicated by the sensor during the irradiation of the sensor with the light and a resistance indicated by the sensor after the stoppage of the light.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

Example 1

Preparation of a Primer Composition and Formation of an Organic Film

As a primer composition, a chemical solution was prepared by mixing 39% by weight of 2-acryloyloxyethyl-phthalic acid (commercially available as HOA-MPL from KYOEISHA CHEMICAL Co., Ltd.), 10% by weight of dimethylaminoethyl methacrylate (commercially available as DM from KYOEISHA CHEMICAL Co., Ltd.), 25% by weight of pentaerythritol acrylate (commercially available as PE-3A from KYOEISHA CHEMICAL Co., Ltd.), 25% by weight of diethyleneglycol dimethacrylate (commercially available as 2EG from KYOEISHA CHEMICAL Co., Ltd.), and 1% by weight of IRGACURE 1173 (manufactured by Ciba Specialty Chemicals, Inc.) as a polymerization reaction initiator so that the total was 100% by weight.

The 2-acryloyloxyethyl-phthalic acid was used as an addition polymerizable compound including an acid group. Dimethylaminoethyl methacrylate was used as an addition polymerizable compound including a basic group. Pentaerythritol acrylate was used as an addition polymerizable compound including three or more reactive groups. Diethyleneglycol dimethacrylate was used as an addition polymerizable compound including a hydrophilic functional group.

The chemical solution was applied onto an acrylic sheet by spin coating. Next, the chemical solution was cured by irradiating it with ultraviolet rays for 20 minutes with an ultraviolet irradiation apparatus (PL16-110, manufactured by SEN LIGHTS CORPORATION), to form an organic film on the acrylic sheet.

Example 2

Formation of a Metal Thin Film

A metal thin film was obtained by subjecting, to the following steps, the acrylic sheet on which the organic film had been formed.
(1) The acrylic sheet was immersed in an 8 M aqueous solution of potassium hydroxide at 60° C. and kept there for 2 minutes.
(2) The acrylic sheet was washed thoroughly in distilled water.
(3) The acrylic sheet was immersed in an aqueous solution of metal ions at room temperature and kept there for 10 minutes. The aqueous solution of metal ions was obtained by mixing together a 100 mM aqueous solution of indium chloride and a 100 mM aqueous solution of sodium acetate with a volume ratio of 1:1.
(4) The acrylic sheet was washed thoroughly in distilled water.
(5) The metal ions were reduced by immersing the acrylic sheet in a 100 mM aqueous solution of sodium borohydride at 40° C. and keeping it there for 10 minutes.
(6) The acrylic sheet was washed thoroughly in distilled water.
(7) The acrylic sheet was dried in a nitrogen atmosphere.

Thus obtained was a metal thin film (having a film thickness of approximately 100 nm) with metallic luster.
(8) The acrylic sheet on which the metal thin film had been formed was kept for 5 hours in an oven at 140° C.

Thus obtained was an element including a transparent indium oxide film with a resistance of approximately 10 kΩ. The resistance was obtained by measuring a surface resistivity with a resistivity meter (Loresta GP; manufactured by Mitsubishi Chemical Corporation).

FIG. 1(a) is a photograph showing a result of observation of a longitudinal section of a sensor according to an embodiment of the present invention by a transmission electron microscope, and FIG. 1(b) is a schematic view of longitudinal sections of a thin-film layer and an organic film in the longitudinal section. As shown in FIGS. 1(a) and 1(b), the indium oxide film is a thin-film layer having a film thickness of approximately 100 nm with a laminate structure of indium oxide particles having a particle diameter of 1 nm to 100 nm.

As shown in FIG. 1(b), the indium oxide film had such a feature as to become smaller in particle diameter from an area near the surface toward the inside (toward the organic film). The indium oxide film was found to take a so-called gradation structure in which the particle diameter of indium oxide particles present in the area near the surface ranges from 50 to 100 nm and the particle diameter becomes smaller toward the inside. As shown in FIG. 1(b), some the indium oxide particles were found embedded in the organic film.

The metal thin film thus obtained through steps (1) to (8) is firmly retained by the organic film without using a binder or the like. Further, although no comparative data are shown, it was found that the metal thin film had its tissue sparser than that of a metal film produced by a conventional publicly-known method such as sputtering and, therefore, was high in electric resistance.

Example 3

Fabrication of a Sensor and Detection of Light Irradiation by the Sensor

Figure 2:
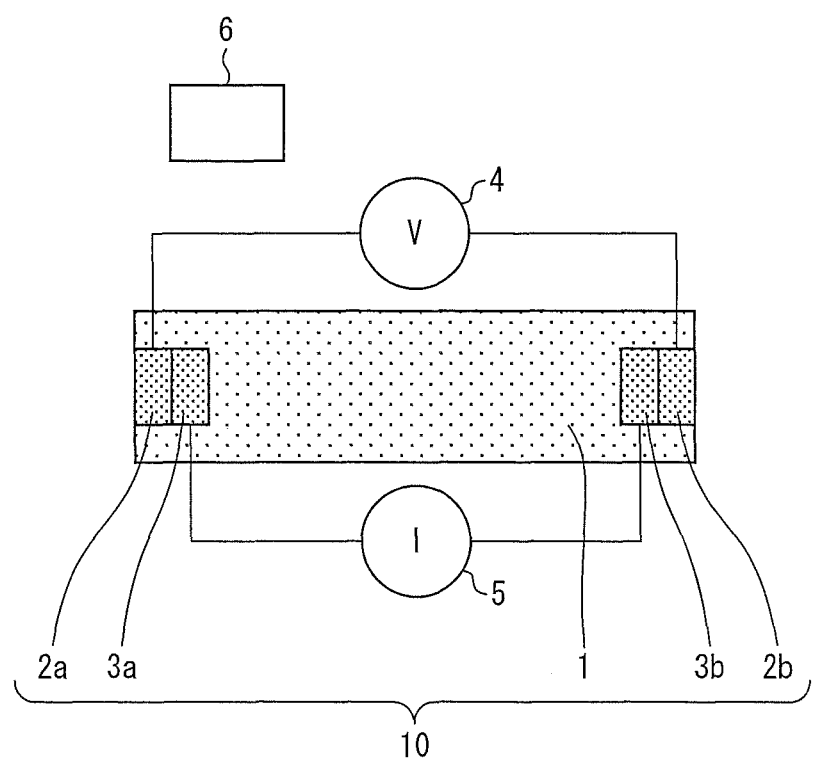
FIG. 2 is a schematic view of the appearance of a sensor according to an embodiment of the present invention.

A circuit which has two outer terminals connected to a power supply and which can detect an electric potential difference with two inner terminals was formed by wiring the four terminals with a conductive paste at both ends of the element. FIG. 2 is a schematic view of the appearance of a sensor 10 according to an embodiment of the present invention thus fabricated. In FIG. 2, the reference sign 1 denotes an element including an organic film or an indium oxide film, the reference signs 2a and 2b denote outer terminals, the reference signs 3a and 3b denote inner terminals, the reference sign 4 denotes a voltmeter, the reference sign 5 denotes an ammeter, and the reference sign 6 denotes a light source. The sensor 10 according to one or more embodiments of the present invention includes the element 1, the outer terminals 2a and 2b, and the inner terminals 3a and 3b. It should be noted that in this specification, the element is sometimes referred to as "sensor".

The light source 6 was placed above the sensor 10. With an electric current of 0.1 mA being passed through each end of the sensor 10, the sensor 10 was evenly irradiated with a light of 50 mW/cm$^2$ from the light source 6 onto an entire surface of the sensor 10 that faced the light source 6 from 10 cm directly above the sensor 10 and, after several seconds, stopped being irradiated.

Figure 3:
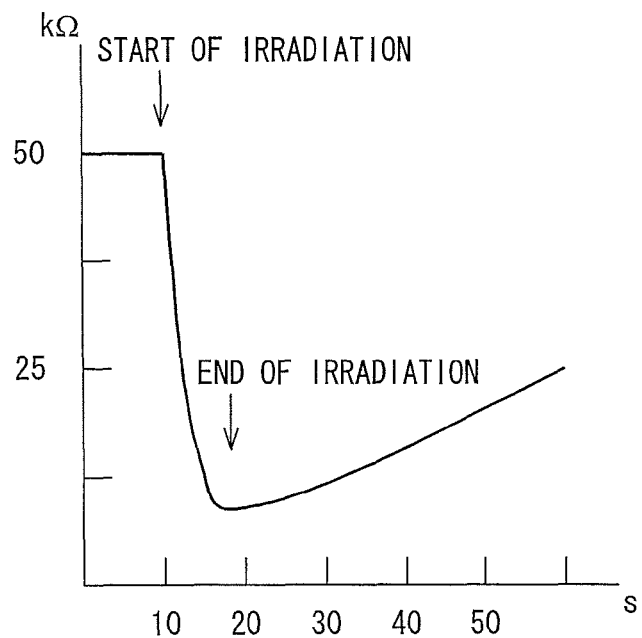
FIG. 3 is a graph showing a change in resistance as exhibited by a sensor according to an embodiment of the present invention in a case where the sensor was irradiated with light and stopped being irradiated.

FIG. 3 is a graph showing a change in resistance as exhibited by the sensor 10 in a case where the sensor 10 was irradiated with light and stopped being irradiated. Upon being irradiated with light for several seconds, the sensor 10 abruptly decreased in resistance. Once the sensor 10 stopped being irradiated, the sensor 10 started to gradually recover in resistance from that point in time.

Because the sensor according to one or more embodiments of the present invention including the indium oxide film formed on the organic film decreases in resistance upon being irradiated with light and recovers in resistance once it stops being irradiated with light, the sensor can detect irradiation with or stoppage of light. Further, it became clear that light irradiation can be easily detected by such a simple structure as that shown in FIG. 2.

Example 4

Detection of Hydrogen by a Sensor

Use of the sensor 10 as a hydrogen gas detection sensor was studied by placing the sensor 10 in an atmosphere of hydrogen gas. The sensor 10 was placed in a container hermetically sealed except for the piping area, and after the container was vacuumed by a rotary pump for several minutes, hydrogen gas was introduced into the container so that 1 atm was attained. Under the condition, the sensor 10 was irradiated with light from the light source 6, placed above the sensor 10, onto an entire surface of the sensor 10 that faced the light source 6 and, after several seconds, stopped being irradiated, as in Example 3.

Figure 4:
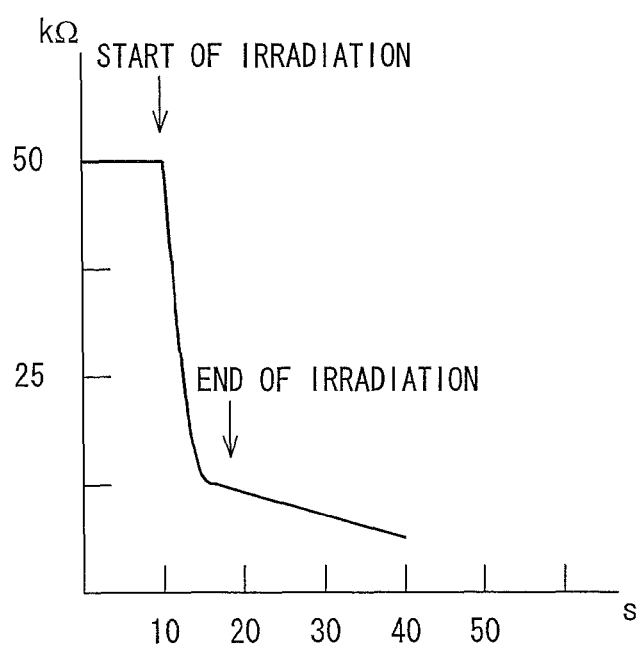
FIG. 4 is a graph showing a change in resistance as exhibited by a sensor according to an embodiment of the present invention in a case where the sensor was irradiated with light in an atmosphere of hydrogen gas and stopped being irradiated.

FIG. 4 is a graph showing a change in resistance as exhibited by the sensor 10 in a case where the sensor 10 was irradiated with light in an atmosphere of hydrogen gas and stopped being irradiated. The sensor 10 showed a tendency similar to that which it showed in Example 3, i.e., showed a tendency to abruptly decrease in resistance upon being irradiated with light for several seconds. In an atmosphere of hydrogen gas, however, the sensor 10 also showed a tendency to decrease in resistance even after it stopped being irradiated with light.

This shows that in an atmosphere where there is no hydrogen as shown in Example 3, the sensor 10 recovers in resistance after stoppage of light irradiation, and that in an atmosphere of hydrogen, the sensor decreases in resistance even after stoppage of light irradiation. Therefore, by utilizing the difference in behavior of the resistance between the presence and absence of hydrogen, the sensor 10 can be used as a hydrogen gas detection sensor.

Example 5

Water Depth Measuring Sensor

Figure 5:
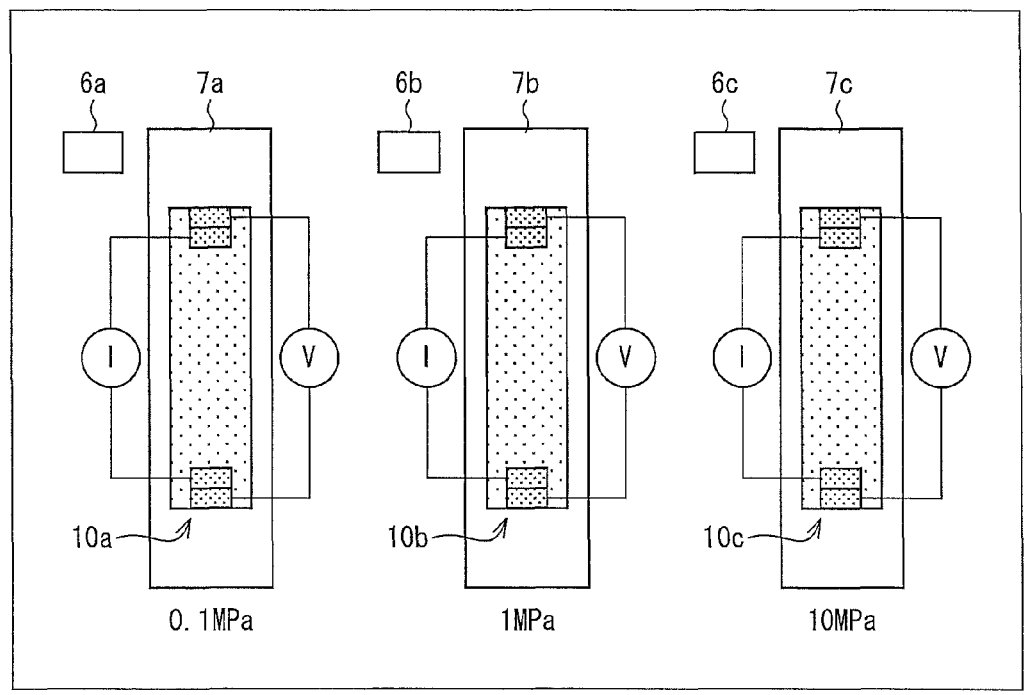
FIG. 5 is a schematic view of sensors according to an embodiment of the present invention each separately encapsulated in hermetically-sealed containers having different degrees of vacuum.

Sensors 10a, 10b, and 10c of an identical structure were encapsulated in hermetically-sealed containers 7a, 7b, and 7c having their inside air pressures kept at 0.1 MPa, 1 MPa, and 10 MPa, respectively, so that the sensors 10 were able to be irradiated with light. FIG. 5 is a schematic view of sensors each separately encapsulated in hermetically-sealed containers having different degrees of vacuum.

As shown in FIG. 5, with an electric current of 0.1 mA being passed through each end of each of the sensors 10a, 10b, and 10c, each of the sensors 10a, 10b, and 10c was evenly irradiated with light from a corresponding one of the light sources 6a, 6b, and 6c onto an entire surface of the sensor 10 which faced the corresponding light source 6 and, after several seconds, stopped being irradiated, as in Example 3. The sensors 10a, 10b, and 10c were all irradiated with light of the same intensity. Because the sensor shown in FIG. 5 is identical in configuration to the sensor shown in FIG. 2, the element and the terminals, which constitute the sensor, are not given reference signs. Further, because the voltmeter and the ammeter are identical to those shown in FIG. 2, they are not given reference signs, either.

Figure 6:
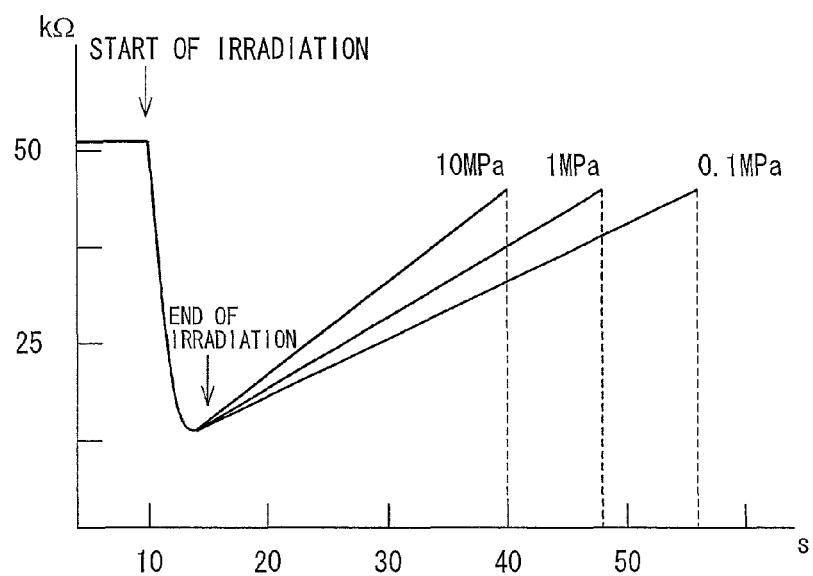
FIG. 6 is a graph showing a difference among times of recovery of resistances as exhibited by sensors each separately encapsulated in hermetically-sealed containers having different degrees of vacuum.

The results are shown in FIG. 6. FIG. 6 is a graph showing a difference among times of recovery of resistances as exhibited by sensors each separately encapsulated in hermetically-sealed containers having different degrees of vacuum.

FIG. 6 shows that a higher air pressure in the container leads to a higher rate of recovery of resistance. This result shows that the time of recovery of resistance changes with changes in air pressure. Utilization of this change allows the sensor according to one or more embodiments of the present invention to be used as an air pressure sensor.

Figure 7:
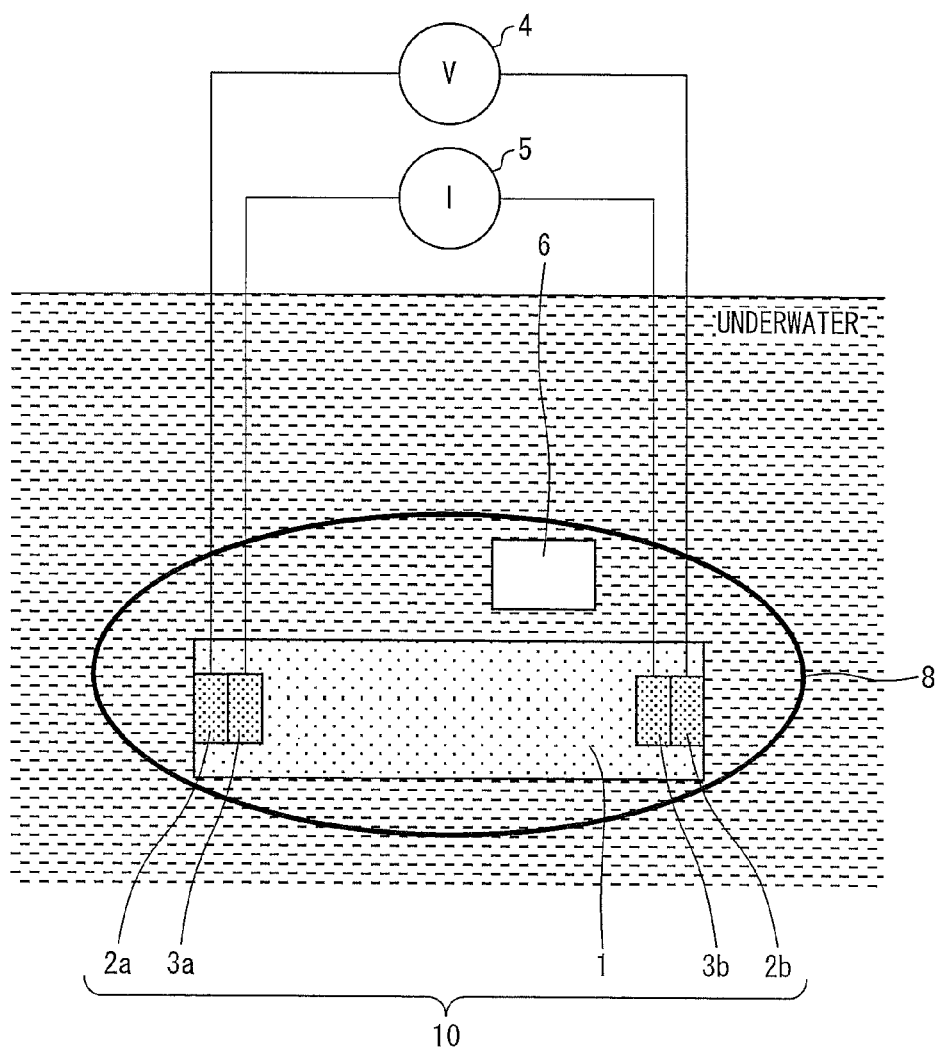
FIG. 7 is a schematic view of a configuration of a water depth measuring sensor based on a sensor according to an embodiment of the present invention.

Further, utilization of this change makes it possible to use a sensor according to one or more embodiments of the present invention, for example, as a water depth measuring sensor. FIG. 7 is a schematic view of a configuration of a water depth measuring sensor based on a sensor according to one or more embodiments of the present invention. In FIG. 7, the reference numeral 8 denotes an elastic body whose inside air pressure changes depending on the ambient pressure. According to one or more embodiments of the present invention, the elastic body is a rubber-like elastic body. The other members identical to those shown in FIG. 2 are given the same reference signs.

As shown in FIG. 7, a rubber-like elastic body 8 in which a sensor 10 and a light source 6 had been encapsulated was submerged in water. Because the ambient water pressure changes with increasing water depth, the elastic body contracts, so that there is a change in air pressure inside of the elastic body. The air pressure inside of the elastic body can be measured by irradiating the sensor 10 with light at a point where it needs to be measured and detecting a tilt of recovery of resistance as exhibited by the element after completion of the irradiation.

There is correlation between the air pressure inside of the elastic body and the water pressure and water depth. Therefore, at various points, correlations between the tilt of recovery of resistance and the air pressure inside of the elastic body are calculated, and correlations between the air pressure inside of the elastic body and the water pressure and water depth are calculated. Then, a calibration curve is created which indicates correlation between the tile of recovery of resistance and the water pressure and water depth. This makes it possible to measure the water depth by using the sensor 10 as a water depth measuring sensor.

Although FIG. 6 shows an embodiment in which the light source 6 is encapsulated in the elastic body 8, a sensor 10 encapsulated in an elastic body 8 may be irradiated with light from outside of the elastic body 8. In this case, for efficient irradiation with light, according to one or more embodiments of the present invention, the elastic body 8 be transparent.

One or more embodiments of the present invention is applicable to an optical sensor, a hydrogen gas detection sensor, an air pressure sensor, and a water depth sensor.

REFERENCE SIGNS LIST

1 Element including organic film and indium oxide film
2a, 2b Outer terminal
3a, 3b Inner terminal
4 Voltmeter
5 Ammeter
6, 6a, 6b, 6c Light source
7a, 7b, 7c Hermetically-sealed container
8 Elastic body
10, 10a, 10b, 10c Sensor

The invention claimed is:

1. A sensor capable of detecting light, hydrogen gas, and air pressure, comprising:
   a metal oxide film formed on a surface of an organic film, the metal oxide film produced by a process comprising:
   (a) forming the organic film by applying a primer composition onto a substrate or a film and then polymerizing the primer composition by
      (I) irradiating, at that surface of the substrate or film onto which the primer composition has been applied, a photopolymerization initiator with light having a wavelength that allows a radical to be produced by the photopolymerization initiator absorbing the light; or
      (II) heating the substrate or film to a temperature at which a thermal polymerization initiator can be decomposed to produce a radical,
      the primer composition comprising:
         (i) an addition polymerizable compound including three or more reactive groups,
         (ii) an addition polymerizable compound including an acid group, and
         (iii) an addition polymerizable compound including a hydrophilic functional group;
   (b) forming a metal (M1) salt from the acid group by treating the organic film with an aqueous solution comprising a metal (M1) ion;
   (c) substituting the metal (M1) salt of the acid group with a metal (M2) salt by treating the organic film, which has been treated with the aqueous solution comprising the metal (M1) ion, with a metal (M2) ion aqueous solution comprising a metal (M2) ion which has a less ionization tendency than the metal (M1) ion;
   (d) reducing the metal (M2) ion so that a metal film is formed on a surface of the organic film; and
   (e) oxidizing the metal film,
   wherein the addition polymerizable compound including three or more reactive groups is at least one type of compound selected from the group consisting of trimethylolpropane triacrylate, pentaerythritol triacrylate, pentaerythritol tetracrylate, dipentaerythritol hexaacrylate, pentaerythritol triacrylate isophorone diisocyanate urethane prepolymer, and dipentaerythritol pentaacrylate hexamethylene diisocyanate urethane prepolymer,
   the addition polymerizable compound including an acid group is at least one type of compound selected from the group consisting of (meth)acrylic acid, vinyl benzenecarboxylic acid, vinyl acetic acid, vinyl sulfonic acid, vinyl benzenesulfonic acid, maleic acid, fumaric acid, an acrylic ester having a phthalic acid group, an acrylic ester having a salicylic acid group, an acrylic ester having an acetylsalicylic acid group, and vinylphenol,
   the addition polymerizable compound including a hydrophilic functional group is at least one type of compound selected from the group consisting of polyethylene glycol diacrylate, polypropylene glycol diacrylate, glycerin diacrylate, polytetramethylene glycol diacrylate, and 2-hydroxypropyl acrylate,
   the metal (M1) is potassium or sodium,
   the metal (M2) is at least one metal selected from the group consisting of indium, zinc and tin,
   the metal oxide film is formed on the surface of the organic film and contains metal oxide particles that are an oxide of the metal (M2) which ranges in particle diameter from 1 nm or larger to 100 nm or smaller, and
   the metal oxide film is such that an average particle diameter of the metal oxide particles across a straight line becomes smaller from a surface of the metal oxide film toward the organic film, the straight line being drawn on a longitudinal section of the sensor in parallel with a surface of the substrate or film on which the organic film has been formed and connecting a left edge with a right edge of the metal oxide film.

2. A water depth measuring sensor comprising:
   a sensor as set forth in claim 1; and
   an elastic body,
   wherein said water depth measuring sensor is obtained by encapsulating the sensor in the elastic body.

3. A method for fabricating a sensor including a metal oxide film, the method comprising:
   (a) forming an organic film by applying a primer composition onto a substrate or a film and then polymerizing the primer composition by
      (I) irradiating, at that surface of the substrate or film onto which the primer composition has been applied, a photopolymerization initiator with light having a wavelength that allows a radical to be produced by the photopolymerization initiator absorbing the light; or
      (II) heating the substrate or film to a temperature at which a thermal polymerization initiator can be decomposed to produce a radical,
      the primer composition containing:
         (i) an addition polymerizable compound including three or more reactive groups,
         (ii) an addition polymerizable compound including an acid group, and
         (iii) an addition polymerizable compound including a hydrophilic functional group;
   (b) forming a metal (M1) salt from the acid group by treating the organic film with an aqueous solution containing a metal (M1) ion;
   (c) substituting the metal (M1) salt of the acid group with a metal (M2) salt by treating the organic film, which has been treated with the aqueous solution containing the metal (M1) ion, with a metal (M2) ion aqueous solution containing a metal (M2) ion which has a less ionization tendency than the metal (M1) ion;
   (d) reducing the metal (M2) ion so that a metal film is formed on a surface of the organic film; and
   (e) obtaining a metal oxide film by oxidizing the metal film,
   wherein the addition polymerizable compound including three or more reactive groups is at least one type of compound selected from the group consisting of trimethylolpropane triacrylate, pentaerythritol triacrylate, pentaerythritol tetracrylate, dipentaerythritol hexaacrylate, pentaerythritol triacrylate isophorone diisocyanate urethane prepolymer, and dipentaerythritol pentaacrylate hexamethylene diisocyanate urethane prepolymer, the addition polymerizable compound including an acid group is at least one type of compound selected from the group consisting of (meth)acrylic acid, vinyl benzenecarboxylic acid, vinyl acetic acid, vinyl sulfonic acid, vinyl benzenesulfonic acid, maleic acid, fumaric acid, an acrylic ester having a phthalic acid group, an acrylic ester having a salicylic acid group, an acrylic ester having an acetylsalicylic acid group, and vinylphenol, the addition polymerizable compound including a hydrophilic functional group is at least one type of compound selected from the group consisting of polyethylene glycol diacrylate, polypropylene glycol diacrylate, glycerin diacrylate, polytetramethylene glycol diacrylate, and 2-hydroxypropyl acrylate, the metal (M1) is potassium or sodium, and, the metal (M2) is at least one metal selected from the group consisting of indium, zinc and tin.

4. A method for detecting irradiation, the method comprising:
   (a) irradiating a sensor with light, the sensor being fabricated by the method set forth in claim 3;
   (b) stopping irradiating the sensor with the light; and
   (c) detecting a difference between a resistance indicated by the sensor during the irradiation of the sensor with the light and a resistance indicated by the sensor after the stoppage of the light.

5. A method for detecting hydrogen gas, the method comprising:
   (a) irradiating a sensor with light in hydrogen gas atmosphere, the sensor being fabricated by the method set forth in claim 3;
   (b) stopping irradiating the sensor with the light; and
   (c) detecting a difference between a resistance indicated by the sensor during the irradiation of the sensor with the light and a resistance indicated by the sensor after the stoppage of the light.

6. A method for measuring air pressure, the method comprising:
   (a) irradiating a sensor with light under different atmospheric pressures, the sensor being fabricated by the method set forth in claim 3;
   (b) stopping irradiating the sensor with the light; and
   (c) detecting, under each of the atmospheric pressures, a difference between a resistance indicated by the sensor during the irradiation of the sensor with the light and a resistance indicated by the sensor after the stoppage of the light.

7. A method for detecting irradiation, comprising:
   irradiating a sensor fabricated by the method as set forth in claim 3 with light;
   stopping irradiating the sensor with the light; and
   detecting a difference between a resistance indicated by the sensor during the irradiation of the sensor with the light and a resistance indicated by the sensor after the stoppage of the light.

8. A method for fabricating a water depth measuring sensor comprising:
   (a) performing the method for fabricating a sensor as set forth in claim 3;
   (b) providing an elastic body;
   (c) encapsulating the sensor of the step (a) in the elastic body.

* * * * *